United States Patent [19]

Borgulya et al.

[11] Patent Number: 5,574,055

[45] Date of Patent: Nov. 12, 1996

[54] OXAZOLIDINONE DERIVATIVES

[75] Inventors: Janos Borgulya, Basel; Hans Bruderer, Biel-Benken, both of Switzerland; Roland Jakob-Roetne; Stephan Rover, both of Inzlingen, Germany

[73] Assignee: Hoffmann-La Roche Inc., Nutley, N.J.

[21] Appl. No.: 349,119

[22] Filed: Dec. 2, 1994

[30] Foreign Application Priority Data

Dec. 13, 1993 [CH] Switzerland ............... 3701/93
Sep. 27, 1994 [CH] Switzerland ............... 2927/94

[51] Int. Cl.⁶ .................................. A61K 31/42
[52] U.S. Cl. ............ 514/376; 514/252; 514/326; 514/338; 544/238; 546/209; 546/271.4; 546/15; 548/232
[58] Field of Search ............. 548/232; 514/376

[56] References Cited

U.S. PATENT DOCUMENTS

| | | | |
|---|---|---|---|
| 3,654,298 | 4/1972 | Douzon et al. | 548/232 |
| 4,150,029 | 4/1979 | Dostert et al. | 548/232 |
| 4,250,318 | 2/1981 | Dostert et al. | 548/232 |
| 4,435,415 | 3/1984 | Bourgery | 548/232 |
| 4,461,773 | 7/1984 | Gregory | 548/232 |
| 4,476,136 | 10/1984 | Dostert et al. | 548/232 |
| 4,517,197 | 5/1985 | Ancher et al. | 548/232 |
| 5,171,747 | 12/1992 | Jarreau et al. | 514/376 |
| 5,182,296 | 1/1993 | Nakai | 514/376 |
| 5,254,577 | 10/1993 | Carlson | 548/232 |
| 5,480,899 | 1/1996 | Yano | 514/376 |

FOREIGN PATENT DOCUMENTS

| | | | |
|---|---|---|---|
| 2381037 | 4/1977 | France. | |
| 2003151 | 8/1978 | United Kingdom. | |
| 2076813 | 5/1981 | United Kingdom | 548/232 |

OTHER PUBLICATIONS

Abstract (corresponding to FRA 2381037) (1977).
Chemistry Letters, 1979 pp. 1277–1278, Published by Chem. Society of Japan.
R. J. Wurtmann and J. A. Axelrod Biochem. Pharmac. 12, 1439–41.

*Primary Examiner*—Donald G. Daus
*Attorney, Agent, or Firm*—George W. Johnston; Robert A. Silverman

[57] ABSTRACT

The present invention relates to compounds of the formula:

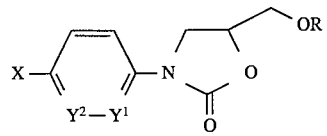

wherein

R is H or alkyl;

$Y^1$ is —CH= or —N=; and $Y^2$ —CH=, —C(OH)=, —C($NO_2$)=, —C($NH_2$)=, —C(Hal)=, —N=;

X is cycloalkenyl; bicyclo[2.2.1]hept-2-yl, optionally substituted by phenyl-2-oxo-5-methoxymethyl-oxazolidinyl; bicyclo[2.2.1]-hept-5-en-2-yl; adamantyl; or cycloalkyl or piperidinyl, optionally substituted by amino, alkyl, —CN, oxo hydroxyimino, ethylenedioxy or by —$OR^1$, $R^1$ is —CH($C_6H_5$)₂, —($CH_2$)ₙ$C_6H_5$, alkyl, H, —($CH_2$)ₙNHCOC$H_3$, —($CH_2$)ₙN$H_2$, —($CH_2$)ₙCN, —($CH_2$)ₙSC$H_3$—($CH_2$)ₙS$O_2$C$H_3$, —CO-lower-alkyl, —COC$_6H_5$, optionally substituted by oxazolidine;

or by =C$R^2R^3$, $R^2$ is alkyl $R^3$ is H, —CN, alkyl, phenyl or COO-alkyl;

or by —($CH_2$)ₙ$R^4$ $R^4$ is —CN, amino, —NHCOC$H_3$, —COC$_6H_5$Hal, phenyl or hydroxy;

or by —CO$R^5$, $R^5$ is alkyl, —CH=CH—$C_6H_5$, —$C_6H_5$, —$C_6H_5CF_3$ or —O-alkyl;

or by —N$R^6R^7$, $R^6$ is or —COC$H_3$;

$R^7$ is —COC$H_3$, benzyl or —($CH_2$)ₙNHCOC$_6H_4$Hal; and n is 1–3;

These can be used for the prevention or control of depressive, panic and anxiety states, and treatment of certain cognitive disorders and neurodegenerative diseases.

18 Claims, No Drawings

OXAZOLIDINONE DERIVATIVES

BRIEF SUMMARY OF THE INVENTION

The present invention relates to a oxazolidin-2-one derivative of the formula

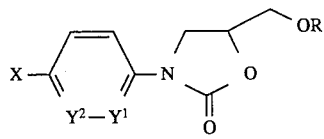

wherein

R is hydrogen or lower alkyl;

X is cycloalkenyl; bicyclo[2.2.1]hept-2-yl, optionally substituted by phenyl-2-oxo-5-methoxymethyloxazolidinyl; bicyclo[2.2.1]-hept-5-en-2-yl; adamantyl; or cycloalkyl or piperidinyl, optionally mono- or multiply-substituted by halogen, amino, lower alkyl, nitrilo, an oxo group, hydroxyimino, ethylenedioxy or by —$OR_1$, in which $R^1$ is —$CH(C_6H_5)_2$, —$(CH_2)_nC_6H_5$, lower alkyl, hydrogen, —$(CH_2)_n NHCOCH_3$, —$(CH_2)_n NH_2$, —$(CH_2)_n CN$, —$(CH_2)_n SCH_3$, —$(CH_2)_n SO_2CH_3$, —CO-lower-alkyl, —$COC_6H_5$ or by =$CR_2R^3$, in which $R^2$ is hydrogen or lower alkyl;

$R^3$ is hydrogen, nitrilo, lower alkyl, phenyl or COO-lower-alkyl;

or by —$(CH_2)_n R^4$, in which $R^4$ is nitrilo, amino, —$NHCOCH_3$, —$COC_6H_5Hal$, phenyl or hydroxy;

or by —$COR^5$, in which $R^5$ is lower alkyl, —CH=CH—$C_6H_5$, —$C_6H_5CF_3$, —O—$C(CH_3)_3$ or —O-lower-alkyl;

or by —$NR^6R^7$, in which $R^6$ is hydrogen or —$COCH_3$;

$R^7$ is —$COCH_3$, benzyl or —$(CH_2)_n NHCOC_6H_4Hal$;

n is 1–3;

$Y^1$ is —CH= or —N=; and $Y^2$ is —CH=, —C(OH)=, —C(NO_2)=, —C(NH_2)=, —C(Hal)= or —N=, and a pharmaceutically acceptable acid addition salt thereof.

The compounds of formula I and their salts possess valuable pharmacological properties, namely monoamine oxidase (MAO) inhibiting properties. The compounds of formula I and their pharmaceutically acceptable salts are useful for the treatment of depressive states, panic and anxiety states, cognitive disorders and neurodegenerative diseases such as Parkinson's disease and Alzheimer's disease.

Objects of the present invention are compounds of formula I and their pharmaceutically acceptable salts, a process for the preparation of these compounds and salts, medicaments containing such a compound or salt and the production of such medicaments, as well as the use of compounds of general formula I and salts defined earlier in the control or prevention of illnesses, especially the control or prevention of depressive states, panic and anxiety states, cognitive disorders and neurodegenerative diseases such as Parkinson's disease and Alzheimer's disease and the use of compounds of formula I and salts defined earlier for the production of medicaments for the control or prevention of depressive states, panic and anxiety states, cognitive disorders and neurodegenerative diseases such as Parkinson's disease and Alzheimer's disease.

DETAILED DESCRIPTION OF THE INVENTION

The invention relates to a compound of the formula

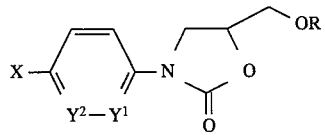

wherein

R is hydrogen or lower alkyl;

$Y^1$ signifies —CH= or —N=; and $Y^2$ signifies —CH=, —C(OH)=, —C(NO_2)=, —C(NH_2)=, —C(Hal)=

X is cycloalkenyl; bicyclo[2.2.1]hept-2-yl, optionally substituted by phenyl-2-oxo-5-methoxymethyloxazolidinyl; bicyclo[2.2.1]-hept-5-en-2-yl; adamantyl; or cycloalkyl or piperidinyl, optionally mono- or multiply-substituted by halogen, amino, lower alkyl, nitrilo, an oxo group, hydroxyimino, ethylenedioxy, —$OR^1$, =$CR_2R^3$, —$(CH_2)_nR^4$, —$COR^5$, or —$NR^6R^7$ wherein $R^1$ is —$CH(C_6H_5)_2$, —$(CH_2)_nC_6H_5$, lower alkyl, hydrogen, —$(CH_2)_n NHCOCH_3$, —$(CH_2)_n NH_2$, —$(CH_2)_n CN$, —$(CH_2)_n SCH_3$, —$(CH_2)_n SO_2CH_3$, —CO-lower-alkyl, —$COC_6H_5$;

$R^2$ is hydrogen or lower alkyl;

$R^3$ is hydrogen, nitrilo, lower alkyl, phenyl or COO-lower-alkyl;

$R^4$ is nitrilo, amino, —$NHCOCH_3$, —$COC_6H_5Hal$, phenyl or hydroxy;

$R^5$ is lower alkyl, —CH=CH—$C_6H_5$, —$C_6H_5CF_3$, —O—$C(CH_3)_3$ or —O-lower-alkyl;

$R^6$ is hydrogen or —$COCH_3$;

$R^7$ is —$COCH_3$, benzyl or —$(CH_2)_n NHCOC_6H_4Hal$; and n is 1–3;

or pharmaceutically acceptable acid addition salt thereof.

The term "lower alkyl" used in the present description denotes straight-chain or branched saturated hydrocarbon residues of 1–7, preferably, 1–4 carbon atoms such as methyl, ethyl, n-propyl, isopropyl, n-butyl, isobutyl, s-butyl, t-butyl and the like.

The term "cycloalkyl" denotes groups derived from saturated cyclic hydrocarbons which preferably contain 3 to 7 ring carbon atoms, such as e.g. cyclopropane, cyclobutane, cyclopentane, cyclohexane or cycloheptane.

The term "cycloalkenyl" denotes groups derived from unsaturated cyclic hydrocarbons which preferably contain 3 to 7 ring carbon atoms, for example, cyclopropenyl, cyclobutenyl, cyclopentenyl, cyclohexenyl, cycloheptenyl or the like.

Hal and halogen are fluorine, chlorine, bromine or iodine.

The term "leaving group" denotes known leaving groups such as halogen, preferably bromine, arylsulfonyloxy, alkylsulfonyloxy and the like.

In accordance with this description reactive carbonyl-yielding agents can be, for example, diethyl carbonate, phosgene or the like.

The term "pharmaceutically acceptable acid addition salt" embraces salts with inorganic and organic acids such as hydrochloric acid, hydrobromic acid, sulfuric acid, phosphoric acid, citric acid, formic acid, maleic acid, acetic acid, succinic acid, tartaric acid, methanesulfonic acid, p-toluenesulfonic acid and the like.

Preferred compounds of formula I are those in which X is cyclohexyl or substituted cyclohexyl, R is hydrogen or methyl and $Y^1$ and $Y^2$ is CH. Preferred cyclohexyl substituents are those such as the oxo group, hydroxy, hydroxyimino, methoxy as well as —O—$(CH_2)_2$—$R^8$ in which $R^8$ signifies —CN or —$CH_2NH_2$. These are for example the following compounds:

(RS)-3-(4-Cyclohexyl-phenyl)-5-hydroxymethyl-oxazolidin-2-one;
(RS)-3-(4-cyclohexylophenyl)-5-methoxymethyl-oxazolidin-2-one;
(R)-3-(4-cyclohexyl-phenyl)-5-methoxymethyl-oxazolidin-2-one;
(RS)-3-[4-(4-oxocyclohexyl)-phenyl]-5-methoxymethyl-oxazolidin-2-one;
(RS)-3-[4-(trans-4-hydroxy-cyclohexyl)-phenyl]-5-methoxymethyl-oxazolidin- 2-one;
(RS)-3-[4-(4-hydroxy-imino-cyclohexyl)-phenyl]-5-methoxymethyl-oxazolidin-2-one;
(R)-3-[4-trans-4-hydroxy-cyclohexyl)-phenyl]-5-methoxymethyl-oxazolidin-2-one;
(RS)-3-[4-(trans-4-methoxy-cyclohexyl)-phenyl]-5-methoxymethyl-oxazolidin-2-one;
(R)-3-[4-(4-oxo-cyclohexyl)-phenyl]-5-methoxymethyl-oxazolidin-2-one;
(RS)-3-[trans-4-[4-(5-methoxymethyl-2-oxo-oxazolidin-3-yl)-phenyl]-cyclohexyloxy]-propionitrile;
acetic acid (RS)-trans-4-[4-(5-methoxymethyl-2-oxo-oxazolidin-3-yl)-phenyl]-cyclohexyl ester;
(RS)-3-[4-(cis- or trans-4-hydroxymethyl-cyclohexyl)-phenyl]-5-methoxymethyl-oxazolidin-2-one; and
(RS)-3-[4-(cis- or trans-4-hydroxy-4-methyl-cyclohexyl)-phenyl]-5-methoxymethyl-oxazolidin-2-one.

Furthermore, also preferred are compounds of formula I in which X is bicyclo[2.2.1]hept-2-yl or bicyclo[2.2.1]hept-5-en-2-yl, for example the compounds
3-[(1RS,2RS,4SR)-4-bicyclo[2.2.1]hept-2-yl-phenyl]-5-methoxymethyl-oxazolidin-2-one and
3-[(1RS,2SR,4RS)-4-bicyclo[2.2.1]-hept-5-en-2-yl-phenyl]-5-methoxymethyl-oxazolidin-2-one.

Likewise preferred are those compounds of formula I in which X is cyclohexyl or piperidinyl, substituted by —$CH_2CN$, —COCH=CH—$C_6H_5$, —O($CH_2$)$NH_2$ or —$OCH_2CN$, R is methyl and $Y^1$ and $Y^2$ is a CH group, for example the following compounds
(RS)-[trans-4-[4-(5-methoxymethyl-2-oxo-oxazolidin-3-yl)-phenyl]-cyclohexyl]-acetonitrile;
(R)-[trans-4-[4-(5-methoxymethyl-2-oxo-oxazolidin-3-yl)-phenyl]-cyclohexyl]-acetonitrile;
(RS)-4-[4-(5-methoxymethyl-2-oxo-oxazolidin-3-yl)-phenyl]-1-(1-oxo-3-phenyl-2-(E)-propenyl)-piperidine;
(RS)-3-(trans-4-[4-(5-methoxymethyl-2-oxo-oxazolidin-3-yl)-phenyl]-cyclohexyloxy)-ethanamine;
(R)-[trans-4-[4-(5-methoxymethyl-2-oxo-oxazolidin-3-yl)-phenyl]-cyclohexyloxy]-acetonitrile;
(RS)-trans-4-[4-(5-methoxymethyl-2-oxo-oxazolidin-3-yl)-phenyl]-cyclohexyloxy]-acetonitrile and
(R)-3-[4-[trans-4-(3-amino-propoxy)-cyclohexyl]-phenyl]-5-methoxymethyl-oxazolidin-2-one.

Compounds of formula I and their pharmaceutically acceptable acid addition salts can be prepared in accordance with the invention by cyclizing a compound of the formula

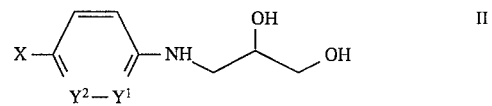

wherein X, $Y^1$ and $Y^2$ have the significances given above, with a reactive carbonyl-yielding agent and, if desired, alkylating a resulting compound of formula I in which R is hydrogen.

The compounds of formula II used as starting materials can be prepared as follows: 4-cyclohexylaniline or other appropriately substituted anilines and methanesulfonic acid (RS)-2,2-dimethyl-1,3-dioxolan-4-ylmethyl ester (described in J. Med. Chem. 27, 1176 [1934]) in triethylamine are held at about 140° C. for a few hours in a bomb tube. Subsequently, after removing the solvent, the residue is stirred with hydrochloric acid, made alkaline and worked up according to usual methods.

A further possibility comprises reacting 4-cyclohexylaniline or other appropriately substituted anilines with [(R)-2,2-dimethyl-1,3-dioxolan-4-methanol toluene-4-sulfonate] in triethylamine at temperatures about 140° C. The mixture is stirred for a few hours and the worked up product is subsequently treated with HCl and, after stirring for about 1 hour, made alkaline with sodium hydroxide solution. The mixture is subsequently worked up according to methods which are known and conventional.

A compound of formula II can be cyclized to a compound of formula I by treatment with a reactive carbonyl-yielding agent. The cyclization is conveniently effected according to methods known per se with diethyl carbonate, with the following procedure being followed: the compound of formula II is dissolved in a solvent, e.g. toluene, treated with diethyl carbonate and, after the addition of a methanolic sodium methylate solution, stirred for several hours while warming. The reaction conditions such as temperature, duration, solvent etc can vary depending on the nature of the reactive derivative used.

A hydroxy group can be alkylated according to known methods. Dimethyl sulfate can conveniently be used as the alkylating agent for a methylation. This can be carried out by dissolving the compound to be alkylated in a suitable solvent, for example toluene, treating the solution with dimethyl sulfate, tetrabutylammonium hydrogen sulfate and a sodium hydroxide solution and stirring intensively. The reaction conditions can vary depending on the alkylating agent and, respectively, the compound to be alkylated.

Compounds of formula I and their pharmaceutically acceptable acid addition salts can be prepared in accordance with the invention by catalytically hydrogenating a benzyl residue, which can be substituted for R in formula I.

A compound of formula I in which a benzyl residue is substituted for R in formula I can be manufactured by reacting a correspondingly substituted cycloalkyl- or piperidinyl-phenyl-ethoxycarbamate with benzyloxymethyl-1,3-dioxolan-2-one according to methods known per se.

A catalytic hydrogenation of benzyl to R=hydrogen can be effected using nickel, platinum or palladium as the catalyst. Suitable solvents for the catalytic hydrogenation are for example water, ethanol, methanol, ethyl acetate, glacial acetic acid or mixtures of these solvents. Conveniently, the benzyl ether is dissolved in methanol and hydrogenated at room temperature with a palladium catalyst. The hydrogenation is effected according to known methods in a shaking apparatus or autoclave.

Compounds of formula I and their pharmaceutically acceptable acid addition salts can be prepared in accordance with the invention by reacting a compound of the formula

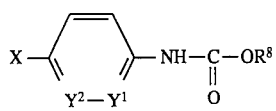

wherein X, Y$^1$ and Y$^2$ have the significances given above and R$^8$ is lower alkyl or benzyl, with a compound of the formula

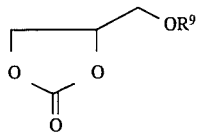

wherein R$^9$ is lower alkyl or benzyl.

Compound III required as the starting material is known and can be prepared as follows.

4-Cycloalkylaniline or other appropriately substituted anilines is/are dissolved in a solvent, for example THF and water, treated with sodium bicarbonate and subsequently reacted with ethyl chloroformate. The reaction temperature should not exceed 20° C.

The compounds of formula IV are known and can be prepared according to literature-known processes.

Conveniently, an alkyl carbamate of formula III is treated with a 4-(alkoxy-methyl)-1,3-dioxolan-2-one IV and the mixture is stirred for several hours while warming.

Compounds of formula I and their pharmaceutically acceptable acid addition salts can be prepared in accordance with the invention by treating a compound of the formula

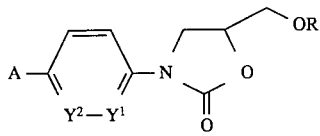

wherein R, Y$^1$ and Y$^2$ have the significances given above and A is a leaving group, with a reactive agent yielding the substituent X.

Compound V can conveniently be prepared as follows, with Y$^2$ in the following example signifying nitrogen:

A mixture of ethyl pyridin-3-ylcarbamate, methoxymethyl-1,3-dioxolan-2-one and potassium carbonate is heated and stirred for a few hours. The resulting compound is treated with an oxidizing agent, preferably 3-chloroperbenzoic acid, whereupon the resulting compound, 5-methoxymethyl-3-(1-oxy-pyridin-3-yl)oxazolidin-2-one is brominated and subsequently converted with a reducing agent, for example phosphorus tribromide, into a compound of formula V. This compound can then be reacted, as described, with a reactive agent yielding the substituent X. Agents which contain, for example, a tributyl-stannyl group as the residue have been found to be suitable. The preparation of these compounds is effected according to known methods.

When A in formula V signifies a halogen atom, especially bromine or iodine, as the leaving group, the reaction can conveniently be carried out as follows: an oxazolidinone of formula V is reacted for several hours in DMF with the addition of triphenylphosphine, bis(triphenylphospine)-palladium-II dichloride, lithium chloride, 2,6-di-tert-butyl-p-cresol and tributyl-cycloalkenylstannane and subsequently worked up according to methods known per se.

Compounds of formula I and their pharmaceutically acceptable acid addition salts can be prepared in accordance with the invention by catalytically hydrogenating a compound of the formula

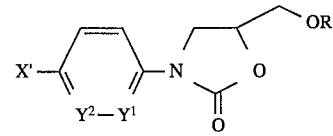

wherein X' is a (C$_5$–C$_7$)-cycloalkenyl residue, which can be substituted as described in formula I for cycloalkyl or piperidinyl, and Y$_1$, Y$^2$ and R have the above significances, to the corresponding saturated cycloalkyl compound.

Substituted cycloalkenyl compounds of formula Ia can be prepared by treating compounds of formula V in which A is a leaving group, preferably halogen, with reactive agents yielding the substituent X' in which X' is a (C$_5$–C$_7$)-cycloalkenyl residue which can be substituted as described in formula I for cycloalkyl. 5- to 7-membered ring systems can be hydrogenated to the cyclopentyl, cyclohexyl or cycloheptyl compounds. The hydrogenation is effected according to known methods conveniently with a palladium catalyst at room temperature and normal pressure. The reactive group can be, for example, the trimethylstannyl group. Conveniently, the reaction is effected under argon in the presence of bis(triphenylphosphine)palladium(II) dichloride in THF according to known methods.

Compounds of formula I and their pharmaceutically acceptable acid addition salts can be prepared in accordance with the invention by hydrolyzing a compound of formula I in which X is cycloalkyl substituted by ethylenedioxy.

A cyclohexyl derivative of formula I substituted by an oxo group is obtained by hydrolyzing according to known methods compounds of formula I in which X is cyclohexyl substituted by ethylenedioxy. It is conveniently dissolved in tetrahydrofuran, stirred with hydrochloric acid for several hours and treated with sodium hydroxide solution.

Compounds of formula I and their pharmaceutically acceptable acid addition salts can be prepared in accordance with the invention by hydrogenating a compound of formula I in which X is a cycloalkyl or piperidinyl residue substituted by —O—(CH$_2$)$_2$—CN, =CH—CN or —CH$_2$CN to the amino compound.

A compound of formula I in which X is cycloalkyl or piperidinyl s substituted by —O—(CH$_2$)$_2$—CN can be hydrogenated to an amino compound according to known methods. Conveniently, a suspension of sodium borohydride, THF and trifluoroacetic acid is treated at room temperature with the corresponding compound of formula I and stirred for several hours. Subsequently, the working up is effected according to usual methods.

When X is cycloalkyl or piperidinyl substituted by an acetonitrile group, the hydrogenation to the amino-ethyl group can be effected in methanolic ammonia in the presence of Raney-nickel. A further variant for obtaining an amino compound of formula I comprises hydrogenating a cycloalkyl or piperidinyl compound substituted by a =CH—CN group with Pd-charcoal and subsequently converting into the amino compound as described above.

When X in formula I is a cycloalkyl or piperidinyl residue substituted by an oxo group, these compounds can be used as starting materials for the manufacture of further compounds of formula I.

When X is, for example, a cycloalkanone, the oxo group can be converted into a hydroxyimino group. This is conveniently carried out according to known methods as follows: an aqueous hydroxylamine solution is added to a corresponding compound of formula I while stirring and cooling. The corresponding hydroxyimino compound separates in crystalline form after the addition of an aqueous sodium carbonate solution.

Furthermore, OH-substituted derivatives of formula I can be obtained when the oxo group is reduced. This can be effected by means of a complex hydride such as, for example, sodium or lithium borohydride in an organic solvent which is inert under the reaction conditions, such as methanol, ethanol or the like. The reduction is conveniently effected at room temperature.

The cycloalkyl or piperidinyl derivatives of formula I substituted by an oxo group can also be reacted with amines, for example with N-(2-aminoethyl)-4-chlorobenzamide, into a —NH(CH$_2$)$_n$NHCOC$_6$H$_4$R$^3$ group, wherein R$^3$ and n have the above significances. Conveniently, the two reaction partners are treated with p-toluenesulfonic acid and dissolved in a toluene/DMF mixture. Subsequently, the mixture is stirred for several hours while warming and, after cooling, treated with sodium borohydride and hydrochloric acid.

Furthermore, compounds of formula I in which X is a cycloalkyl or piperidinyl residue substituted by an oxo group can be converted into methylene-, benzylidene-, dimethylmethylene-, methylene-nitrilo- or methoxycarbonylmethylene-substituted cycloalkyl or piperidinyl derivatives.

This is conveniently carried out as follows: methyltriphenylphosphonium bromide/sodium amide mixtures or isopropyltriphenylphosphonium bromide/sodium amide mixtures or benzyltriphenylphosphonium bromide/sodium amide mixtures or methoxycarbonylmethylenetriphenylphosphonium bromide/sodium amide mixtures are suspended in THF under argon and stirred. The corresponding oxo-cycloalkyl or oxo-piperidinyl compound of formula I is added thereto and stirred for several hours while warming. The working up is effected according to usual methods. If desired, the methylene group can be subsequently hydrogenated.

Compounds of formula I in which X is a cycloalkyl or piperidinyl residue substituted by an ethylenedioxy group can also be prepared. Conveniently, a correspondingly substituted oxo-cycloalkyl or oxo-piperidinyl compound of formula I is reacted with ethylene glycol in the presence of p-toluenesulfonic acid monohydrate in toluene. The target compounds result after stirring for several hours while warming and usual working up.

A cycloalkyl or piperidinyl residue substituted by an oxo group can be converted into a corresponding residue substituted by an amino group by conveniently reacting the corresponding oxo compound with benzylamine and toluenesulfonic acid and subsequently hydrogenating for several hours with sodium borohydride at room temperature.

An oxo-cyclohexyl group can also be converted into —CH—CN, for example, a cyclohexylidene-acetonitrile group, by conveniently dissolving sodium in ethanol and treating this solution with a phosphonate, for example, an ethanolic diethyl cyanomethylphosphonate solution. Subsequently, the reaction with a corresponding oxo-cyclohexyl compound of formula I is effected to give the target compound.

When X in formula I is a cycloalkyl or piperidinyl residue substituted by a hydroxy group, these compounds can also be used as starting materials for the manufacture of further compounds of formula I. Nitrilo-substituted compounds (—O(CH$_2$)$_2$CN) can be manufactured, for example, by reacting hydroxy-cycloalkyl or piperidinyl derivatives of formula I with acrylonitrile in the presence of potassium tert-butylate.

The nitrilo-substituted compounds of formula I obtained in this manner can, if desired, be converted into corresponding amino compounds by alkylation or acylation with corresponding alkyl, aryl or acyl halides, for example by treating them with dry ammonia gas, dissolved in methanol, and hydrogenating in the presence of Raney-nickel.

Compounds of formula I which contain a hydroxy group can be acylated with acid chlorides to the corresponding carbonyloxy compounds. Conveniently, the cycloalkyl or piperidinyl compound of formula I substituted by a hydroxy group is dissolved in a solvent, for example methylene chloride, this solution is treated with pyridine and an acid chloride, for example acetyl chloride or benzoyl chloride, and stirred at room temperature for several hours. The working up is effected according to usual methods.

An alkylation or acylation of compounds of formula I which contain a hydroxy group can be carried out with corresponding alkyl or acyl halides, for example with methyl iodide, benzyl bromide or chlorodiphenylmethane. These reactions are effected according to known methods.

A halogenation of compounds of formula I which contain a hydroxy group can also be effected according to known methods using a suitable halogenating agent. For example, the fluoro-cycloalkyl compound of formula I is obtained by reacting the hydroxy-cycloalkyl compound with a mixture of diethylamino-sulfur trifluoride and methylene chloride after stirring at room temperature.

Compounds which contain a hydroxy group can be converted, also according to process variant j), into corresponding sulfanyl compounds. This can be conveniently effected by dissolving the hydroxy compound in dimethyl sulfoxide and then treating with glacial acetic acid and acetic anhydride and stirring at room temperature for several hours. This and other methods are described in "Chemistry letters", 1979, pp 1277–1278, published by the Chemical Society of Japan.

If desired, the corresponding sulfinyl compound can be obtained by oxidizing the sulfanyl compound subsequently to the above-described variant. Sodium periodate is, for example, well suited as the oxidizing agent.

The corresponding sulfonyl compound can be obtained by oxidizing the sulfanyl compound, with chloroperbenzoic acid being conveniently used as the oxidizing agent. Methylene chloride is, for example, a suitable solvent.

Compounds of formula I in which X is a cycloalkyl residue substituted by a hydroxy group are dehydrogenated to a cycloalkenyl residue conveniently by reacting the hydroxy compound with triphenylphosphine and benzoic acid in tetrahydrofuran at room temperature and subsequently treating with diethyl azodicarboxylate.

In the case of a compound of formula I in which X is a cycloalkyl or piperidinyl residue substituted by a —O(CH$_2$)$_n$—SOCH$_3$— group, this group is converted into a —O(CH$_2$)$_n$CN group by dissolving the corresponding sulfinyl compound in a solvent, for example tetrahydrofuran, and reacting in the presence of zinc iodide and trimethylsilyl cyanide. This reaction takes place over several hours at room temperature.

A compound of formula I in which X is a piperidinyl or protected piperidinyl residue, which is not linked via a nitrogen atom, or a cycloalkyl residue, can be acylated with suitable acylating agents, for example with benzyl bromide, ω-chloro-4-fluorobutyrophenone, trifluoromethylbenzoyl chloride, acetic anhydride or cinnamyl chloride according to known methods. Dimethylformamide or methylene chloride is an especially suitable solvent.

Compounds of formula I which contain a methylene group as the cycloalkyl or piperidinyl substituent can also be used as starting materials for the manufacture of further compounds of formula I.

A corresponding compound of formula I in which X is a cycloalkyl or piperidinyl residue substituted by a methylene group can be converted into a hydroxymethyl-substituted compound by hydroborating this compound, dissolved in a solvent, for example THF, with sodium borohydride in the presence of dimethyl sulfate and oxidizing the intermediate with $H_2O_2$.

The 4-methylene-substituted cycloalkyl compounds of formula I can also be converted into corresponding 4-hydroxy-4-methyl-substituted cycloalkyl or piperidinyl derivatives. For this purpose, mercuric acetate is dissolved in THF and treated with the 4-methylene-substituted cycloalkyl compound of formula I. The mixture is stirred at room temperature, treated with sodium hydroxide solution and reacted with sodium borohydride. The working up is effected in the usual manner.

The pharmaceutically usable salts can be manufactured readily according to known methods having regard to the state of the art and taking into consideration the nature of the compound to be converted into a salt.

As mentioned earlier, the compounds of formula I and their pharmaceutically acceptable acid addition salts have monoamine oxidase (MAO)) inhibiting activity. The compounds of formula I and their salts can be used for the treatment of depressive states, panic and anxiety states, cognitive disorders and neurodegenerative diseases. Examples of such diseases are parkinsonic age-related memory impairment, primary and secondary degenerative dementia, for example dementia of the Alzheimer type or multi-infarct caused dementia and cerebrovascular disorders and consequences of cerebral damage.

The MAO inhibiting activity of the compounds in accordance with the invention can be determined using standard methods.

The preparations to be tested were investigated in the in vitro test described hereinafter, which was based on the method of R. J. Wurtmann and J. A. Axelrod [Biochem. Pharmac. 12, 1439–41 (1963).

Isolated rat brains are homogenized in 0.1 molar potassium phosphate buffer (pH 7.4) in the ratio 1:9 (weight/volume), whereupon the homogenate is diluted with the same buffer in the ratio 1:4 (volume/volume) and stored at −20° C. A mixture of the following composition is used for the incubation:

100 µl of 1M phosphate buffer (pH 7.4);

100 µl of solubilizate of the substance to be tested in water or in aqueous dimethyl sulfoxide;

50 µl of rat brain homogenate; and as the substrate

50 µl of $^{14}C$-labelled serotonin (5-HT) or $^{14}C$-phenylethylamine (PEA), in each instance 100,000 decay per minute, corresponding to a final concentration of $2·10^{-4}$ mol/l and, respectively, $2·10^{-5}$ mol/l.

A pre-incubation at 37° C. is effected for 30 minutes prior to the addition of the substrate. The incubation (in the presence of the substrate) is likewise effected at 37° C. and lasts for 10 minutes. The reaction is stopped by the addition of 200 µl of 2N hydrochloric acid. In order to extract the deaminated product, the mixture is shaken for 10 minutes with 5 ml of diethyl ether or with 5 ml of n-heptane depending on whether 5-HT or PEA is used as the substrate, whereupon the mixture is centrifuged, the aqueous phase is frozen in a dry-ice bath and the organic phase is transferred into a counting glass.

The activity of the MAO in comparison to the control homogenates is determined on the basis of the β-counter values.

Under the above test conditions the activity is linear with respect to time and to the concentration of the homogenizate.

The $IC_{50}$ values were determined graphically as a log of the concentration-activity curve. The $IC_{50}$ was defined as that concentration of a substance to be tested which reduces the activity of the MAO upon the substrate 5-HT or PEA by 50%.

The following Table sets forth the $IC_{50}$ values of compounds in accordance with the invention.

TABLE 1

| Example No. | MAO inhibition in vitro (brain) $IC_{50}$ in nmol/l |
|---|---|
| Befloxaton | 1.9 |
| 1 | 8.5 |
| 2 | 2.0 |
| 6 | 0.1 |
| 7 | 10.0 |
| 8 | 8.4 |
| 9 | 6.0 |
| 14 | 1.0 |
| 15 | 8.5 |
| 16 | 6.0 |
| 18 | 9.0 |
| 30 | 5.0 |
| 33 | 10.0 |
| 38 | 3.0 |
| 39 | 4.0 |
| 49 | 0.9 |
| 50 | 1.0 |
| 59 | 10.0 |
| 63 | 1.6 |
| 66 | 2.0 |
| 68 | 74.0 |
| 71 | 33.0 |

The compounds of formula I as well as their pharmaceutically acceptable acid addition salts can be used as medicaments, for example in the form of pharmaceutical preparations. The pharmaceutical preparations can be administered orally, for example in the form of tablets, coated tablets, dragées, hard and soft gelatine capsules, solutions, emulsions or suspensions. The administration can, however, also be effected rectally, for example in the form of suppositories, or parenterally, for example in the form of injection solutions.

The compounds of formula I and their pharmaceutically acceptable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients for example for tablets, dragées and hard gelatine capsules.

Suitable excipients for soft gelatine capsules are for example vegetable oils, waxes, fats, semi-solid and liquid polyols and the like.

Suitable excipients for the manufacture of solutions and syrups are for example water, polyols, saccharose, invert sugar, glucose and the like.

Suitable excipients for injection solutions are for example water, alcohols, polyols, glycerol, vegetable oils and the like.

Suitable excipients for suppositories are for example natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention compounds of formula I as well as their pharmaceutically acceptable acid addition salts can be used in the control or prevention of depressive states, cognitive disorders and neurodegenerative diseases such as Parkinson's disease and Alzheimer's disease. The dosage can vary within wide limits and will, of course, be fitted to the individual requirements in each particular case. In general, in the case of oral administration a daily dosage of about 10 to 100 mg of a compound of formula I should be appropriate, although the upper limit just given can also be exceeded when this is shown to be indicated.

The following Examples illustrate the present invention, but are not intended to be limiting in any manner. All temperatures are given in degrees Celsius.

EXAMPLE 1

(RS)-3-(4-Cyclohexyl-phenyl)-5-hydroxymethyl-oxazolidin-2-one 2.4 g (9.62 mmol) of (RS)-3-(4-cyclohexyl-phenylamino)-propane-1,2-diol were dissolved in 50 ml of toluene, treated with 1.25 g (10.6 mmol) of diethyl carbonate and 0.4 ml of a 1 molar sodium methylate solution in methanol and stirred overnight at an oil bath temperature of 110°. The solvent was distilled off in a water-jet vacuum and the residue was treated with water and 1N hydrochloric acid and extracted with ethyl acetate. The organic phase was washed with water, dried over magnesium sulfate and the solvent was distilled off. 1.4 g of product in the form of yellowish crystals were obtained from ethyl acetate/hexane. A further 0.9 g of pure product was obtained from the mother liquor. M.p.: 167°–167.5°.

EXAMPLE 2

(RS)-3-(4-Cyclohexyl-phenyl)-5-methoxymethyl-oxazolidin-2-one 1.5 g (5.45 mmol) of (RS)-3-(4-cyclohexyl-phenyl)-5-hydroxymethyl-oxazolidin-2-one were treated with 15 ml of toluene, 1.6 ml of dimethyl sulfate (16.3 mmol), 185 mg of tetrabutylammonium hydrogen sulfate and a solution of 1.09 g (27.2 mmol) of sodium hydroxide in 1.3 ml of water and stirred intensively for 30 minutes. The reaction mixture was poured into ice-water and extracted with ethyl acetate, the organic phase was washed with water, dried over magnesium sulfate and the solvent was distilled off. 1.6 g of a yellow oil were obtained. 0.7 g of colorless crystals was obtained after treatment with ethyl acetate/hexane. M.p.: 69°–70°.

EXAMPLE 3

(S)-3-(4-Cyclohexyl-phenyl)-5-hydroxymethyl-oxazolidin-2-one

A solution of 1.40 g (5.6 mmol) of (S)-3-(4-cyclohexyl-phenylamino)-propane-1,2-diol in 50 ml of toluene was treated with 0.73 g (6.2 mmol) of diethyl carbonate and 0.5 ml of a 1 molar sodium methylate solution and stirred overnight at an oil bath temperature of 110°. After distilling off the solvent the residue was treated with water and 5 ml of 1N hydrochloric acid and extracted with ethyl acetate. The organic phase was washed with sodium chloride solution, dried over magnesium sulfate and the solvent was distilled off. 1.35 g of (S)-3-(4-cyclohexylphenyl)-5-hydroxymethyl-oxazolidin-2-one were obtained in the form of colorless crystals from ethyl acetate/hexane. M.p.: 166°–168°. $[\alpha]_D=+51.25°$ (c=0.8/CH$_3$OH).

EXAMPLE 4

(S)-3-(4-Cyclohexyl-phenyl)-5-methoxymethyl-oxazolidin-2-one 250 mg of tetrabutylammonium dihydrogen sulfate, a solution of 0.73 g of sodium hydroxide (18.2 mmol) in 1 ml of water and 1.1 ml of dimethyl sulfate (10.9 mmol) were added to a solution of 1.0 g (3.63 mmol) of (S)-3-(4-cyclohexyl-phenyl)-5-hydroxymethyl-oxazolidin-2-one in 10 ml of toluene and stirred at 110° for 1 hour. After cooling the mixture was treated with 10 ml of water and extracted with ethyl acetate. After concentrating the solvent there were obtained 1.2 g of a crystalline mixture which was chromatographed on a 30-fold amount of silica gel. The tlc-uniform ethyl acetate-hexane (1:1) fractions were pooled and the solvent was distilled off. 0.85 g of (S)-3-(4-cyclohexylphenyl)-5-methoxymethyl-oxazolidin-2-one was obtained in the form of colorless crystals. M.p.: 90°–92°. $[\alpha]_D=+39.7°$ (c=0.7/CHCl$_3$).

EXAMPLE 5

(R)-3-(4-Cyclohexyl-phenyl)-5-hydroxymethyl-oxazolidin-2-one 6.2 g (24.8 mmol) of (R)-3-(4-cyclohexyl-phenylamino)-propane-1,2-diol were reacted and worked up as given in Example 3. 6.3 g (93%) of beige crystals were obtained. M.p.: 166°–168°. $[\alpha]_D=-48.9°$ (c=0.7/CH$_3$OH).

EXAMPLE 6

(R)-3-(4-Cyclohexyl-phenyl)-5-methoxymethyl-oxazolidin-2-one 2.0 g (7.26 mmol) of (R)-3-(4-cyclohexyl-phenyl)-5-hydroxymethyl-oxazolidin-2-one were reacted and worked up as given in Example 4. 1.91 g (91%) of (R)-3-(4-cyclohexyl-phenyl)-5-methoxymethyl-oxazolidin-2-one were obtained in the form of colorless crystals. M.p.: 86°–88°. $[\alpha]_D=-37.7°$ (c=0.3/CHCl$_3$).

EXAMPLE 7

(RS)-3-[4-(4-Oxo-cyclohexyl)-phenyl]-5-methoxymethyl-oxazolidin-2-one 10.0 g (38.3 mmol) of [4-(4-oxo-cyclohexyl)-phenyl]-ethoxycarbamic ester, 10.0 g (75 mmol) of (RS)-4-(methoxymethyl)-1,3-dioxolan-2-one and 0.5 g of potassium carbonate were stirred intensively for 4 hours at an oil bath temperature of 160°. After cooling the mixture was treated with 50 ml of water and extracted with ethyl acetate. The yellow oil (15.5 g) which separated after distillation of the solvent was chromatographed on a 30-fold amount of silica gel. The methylene chloride/ethyl acetate (15:1) fractions which were uniform by tlc (ethyl acetate/hexane 7:3) were pooled and the solvent was distilled off. 5.54 g (48%) of a colorless product were obtained. M.p.: 114°–116°.

EXAMPLE 8

(RS)-3-[4(trans-4-Hydroxy-cyclohexyl)-phenyl]-5-methoxymethyl-oxazolidin-2-one 5.0 g (16.44 mmol) of (RS)-5-methoxymethyl-3-[4-(4-oxo-cyclohexyl)-phenyl]-oxazolidin-2-one were dissolved in 150 ml of ethanol while heating and, after cooling, treated while stirring with 620 mg (16.4 mmol) of sodium borohydride, cooled overnight and the solvent was subsequently distilled off. The oily residue obtained was treated with water and 1N hydrochloric acid and the reaction product was taken up in ethyl acetate. The organic phase was washed with water, dried over magnesium sulfate and the solvent was distilled off. The colorless oil obtained (5.3 g) was dissolved in ethyl acetate, treated with hexane until turbid and the separated precipitate was filtered off under suction after 1 hour. 3.3 g of an alcohol which was uniform in the nmr spectrum were obtained. M.p. 109°–110°.

EXAMPLE 9

(RS)-3-[4-(4-Hydroxy-imino-cyclohexyl)-phenyl]-5-methoxymethyl-oxazolidin-2-one

The oxime prepared from the ketone in a conventional manner was recrystallized from ethyl acetate. M.p. 146°–147°.

EXAMPLE 10

(RS)-5-Benzyloxymethyl-3-[4-(4-oxo-cyclohexyl)-phenyl]-oxazolidin-2-one 20 g (76.5 mmol) of [4-(4-oxo-cyclohexyl)-phenyl]-ethoxycarbamic ester, 23.8 g of (RS)-4-(benzyloxymethyl)-1,3-dioxolan-2-one and 0.25 g of potassium carbonate were stirred intensively for 3 hours and worked up and chromatographed as given in Example 7. The benzyl ether obtained was recrystallized from t-butyl methyl ether/hexane. M.p.: 126.5°–128°.

EXAMPLE 11

(RS)-5-Hydroxymethyl-3-[4-(4-oxo-cyclohexyl)-phenyl]-oxazolidin-2-one 4.9 g (12.9 mmol) of (RS)-5-benzyloxy-3-[4-(4-oxo-cyclohexyl)-phenyl]-oxazolidin-2-one were dissolved in 500 ml of ethanol while heating and, after adding 5% Pd/C, hydrogenated at room temperature. After separating the catalyst the solvent was distilled off and the oil obtained was chromatographed on a 30-fold amount of silica gel. The methylene chloride-ethyl acetate (1:4) eluates were pooled and the solvent was distilled off. 3.2 g of product were obtained from ethyl acetate/hexane. M.p.: 151.5°–152.5°.

EXAMPLE 12

(RS)-3-[4-(trans-Hydroxy-cyclohexyl)-phenyl]-5-hydroxymethyl-oxazolidin-2-one

As given in Example 8, 0.5 g (1.73 mmol) of (RS)-5-hydroxymethyl-3-[4-(4-oxo-cyclohexyl)-phenyl]-oxazolidin-2-one were dissolved in 500 ml of ethanol and reduced with 65 mg (1.73 mmol) of sodium borohydride and worked up. A crystalline product (0.38 g) was obtained. M.p.: 180°–182°.

EXAMPLE 13

(RS)-3-(4-Cyclopropyl-phenyl)-5-methoxymethyl-oxazolidin-2-one 3.0 g (10.48 mmol) of (RS)-5-methoxymethyl-3-(4-bromo-phenyl)-oxazolidin-2-one, 6.29 g (6.29 mmol) of triphenylphosphine, 0.88 g (1.25 mmol) of bis(triphenylphosphine)palladium-II dichloride, 3.73 g of lithium chloride, 1 spatula tip of 2,6-di-tert-butyl-p-cresol and 6.94 g of tributyl-cyclopropylstannane in 50 ml of DMF were stirred at 120° for 6 hours. The reaction mixture was treated with water and 1N sodium hydroxide solution and extracted with ether. The crude product obtained was chromatographed on a 30-fold amount of silica gel. The extracts which were uniform according to tlc (silica gel, ethyl acetate-hexane 1:1) were pooled and the solvent was distilled off. 0.3 g of colorless crystals was obtained from tert-butyl methyl ether/hexane. M.p. 58°–60°.

EXAMPLE 14

(R)-3-[4-(4-Oxo-cyclohexyl)-phenyl]-5-methoxymethyl-oxazolidin-2-one

As given in Example 7, 5.0 g (19.13 mmol) of [4-(4-oxo-cyclohexyl)-phenyl]-ethoxycarbamic ester are reacted with 3.0 g of (S)-4-methoxymethyl-1,3-dioxolan-2-one and worked up. 1.25 g of product were obtained in the form of yellowish crystals from tert-butyl methyl ether/hexane. M.p. 92°–93°, $[\alpha]_D=-38.1$ (c=1, $CHCl_3$).

EXAMPLE 15

(R)-3-[4-(trans-4-Hydroxy-cyclohexyl)-phenyl]-5-methoxymethyl-oxazolidin-2-one

As given in Example 8, 1.0 g of ketone are reduced with sodium borohydride in ethanol and worked up. 0.7 g of colorless crystals was isolated from ethyl acetate/hexane. M.p. 133.5°–134.5°. $[\alpha]_D=-38.6°$ (c=0.7, $CHCl_3$).

EXAMPLE 16

(RS)-3-[4-(trans-4-Methoxy-cyclohexyl)-phenyl-5-methoxymethyl-oxazolidin-2-one 0.5 g (1.64 mmol) of (RS)-3-[4-trans-4-hydroxy-cyclohexyl)-phenyl]-5-methoxymethyl-oxazolidin-2-one was dissolved in 5 ml of dimethylformamide, treated with 0.51 ml (8.2 mmol) of methyl iodide and 107 mg (2.46 mmol) of sodium hydride dispersion (55%) and stirred at 400 overnight. The reaction mixture was poured into ice-water and extracted with ether. The organic phases were washed with water, dried over magnesium sulfate and the solvent was distilled off. The gel obtained was chromatographed on a 30-fold amount of silica gel with methylene chloride/ethyl acetate (1:4). Crystallization took place upon treatment with tert-butyl methyl ether/hexane. 0.33 g of product was obtained. M.p. 82°–83°.

EXAMPLE 17

3-[(1RS,2RS,4SR)-4-Bicyclo[2.2.1]-hept-2-yl-phenyl]-5-methoxymethyl-oxazolidin-2-one (R:S=1:1)

A solution of 56 mg of bis-(triphenylphosphine)-palladium (II) diacetate, 0.5 g of (RS)-3-(4-iodophenyl)-5-methoxymethyl-oxazolidin-2-one, 0.16 g of bicyclo[2.2.1]hept-2-ene, 0.5 ml of piperidine, 1 ml of dimethylformamide and 0.15 ml of formic acid was stirred for 3 hours under an argon atmosphere. The reaction mixture was diluted with 50 ml of ethyl acetate and the separated precipitate was removed. The filtrate was extracted twice with 20 ml of water each time, the organic phase was dried over magnesium sulfate and the solvent was distilled off. The brown oil obtained was chromatographed on a 30-fold amount of silica gel with ethyl acetate/hexane (7:3), with 0.43 g of uniform product being obtained after crystallization in ethyl acetate/hexane while cooling. The racemic (1:1) diastereomer mixture melted at 83°–84°.

EXAMPLE 18

3-[(1RS,2SR,4RS)-4-Bicyclo[2.2.1]hept-5-en-2-yl-phenyl]-5-methoxymethyl-oxazolidin-2-one (R:S=1:1)

1.0 g of (RS)-3-(4-iodophenyl)-5-methoxymethyl-oxazolidin-2-one was reacted and worked up as described in Example 17. 0.37 g of racemic (1:1) diastereomer mixture was obtained in the form of a crystalline product. M.p. 46°–48°.

EXAMPLE 19

Mixture of (RS)- and (SR)-5-methoxymethyl-3-[4-[-(RS)-3-oxo-cyclopentyl]-phenyl]-oxazolidin-2-one A suspension of 0.44 g of (RS)-3-(4-iodo-phenyl)-5-methoxymethyl-2-oxazolidinone and 15 mg of tetrakis(triphenylphosphine)palladium in 1.1 ml of 2-cyclopentenone and 1.8 ml of triethylamine was stirred at 80° C. under argon for 24 h. The reaction mixture was cooled and, after adding 100 ml of 2N hydrochloric acid, extracted with ethyl acetate. The organic phase was dried with magnesium sulfate and concentrated. The residue (0.6 g of brown oil) was chromatographed over silica gel 60 with ethyl acetate/hexane mixtures (1:3–1:1) and yielded 0.26 g of (RS)- and (SR)-5-methoxymethyl-3-[4-[(RS)-3-oxo-cyclopentyl]-phenyl]-oxazolidin-2-one as a colorless oil. $^1$H-nmr (CDCl$_3$) ppm: 7.53 (d, 2H), 7.26 (d, 2H), 4.76 (m, 1H), 4.06 (t, 1H), 3.93 (t, 1H), 3.65 (d, 2H), 3.44 (s, 3H), 3.40 (m, 1H), 2.65 (m, 1H), 2.36 (m, 4H), 1.98 (m, 1H).

EXAMPLE 20

(RS)-5-Methoxymethyl-3-[4-(4-oxo-piperidin-1-yl)phenyl]-oxazolidin-2-one

A mixture of 6.0 g of ethyl 4-(4-oxo-piperidin-1-yl)-phenylcarbamate, 5.0 g of 4-methoxymethyl-1,3-dioxolan-2-one and 0.6 g of potassium carbonate was heated to 160° C. under argon for 3 h. The reaction mixture was cooled, treated with methylene chloride and water and the phases were separated. The organic phase was dried with magnesium sulfate and concentrated. The residue (7.8 g) was chromatographed over silica gel 60 using ethyl acetate as the eluent. There was obtained 0.6 g of (RS)-5-methoxymethyl-3-[4-(4-oxo-piperidin-1-yl)-phenyl]-oxazolidin-2-one.
$^1$H-nmr (CDCl$_3$) ppm: 7.46 (d, 2H), 6.98 (d, 2H), 4.76 (m, 1H), 3.99 (t, 1H), 3.88 (t, 1H), 3.64 (d, 2H), 3.57 (t, 4H), 3.44 (s, 3H), 2.56 (t, 4H).

EXAMPLE 21

(RS)-3-[4-(4-Hydroxy-piperidin-1-yl)-phenyl]-5-methoxymethyl-2-oxazolidin-2-one 0.3 g of sodium borohydride was added to a solution of 0.6 g of (RS)-5-methoxymethyl-3-[4-(4-oxo-piperidin-1-yl)-phenyl]-oxazolidin-2-one in 25 ml of methanol and 2.5 ml of water. This mixture was stirred at room temperature for 24 h. and subsequently concentrated. The residue was taken up with methylene chloride and washed with 10% aqueous ammonia solution. The organic phase was dried with magnesium sulfate and concentrated. The residue (0.6 g) was chromatographed over silica gel 60 with ethyl acetate/hexane mixtures (1:1–2:1). Crystallization from ethyl acetate yielded 0.1 g of (RS)-3-[4-(4-hydroxy-piperidin-1-yl)-phenyl]-5-methoxymethyl-2-oxazolidin-2-one. M.p.: 149°–152°.

EXAMPLE 22

(RS)-3-[5-(1,4-Dioxa-Spiro[4,5]decan-8-yl)-pyridin-2-yl]-5-methoxymethyl-oxazolidin-2-one A solution of 0.9 g of (RS)-3-[5-(1,4-dioxa-spiro[4,5]dec-7-en-8-yl)-pyridin-2-yl]-5-methoxymethyl-oxazolidin-2-one and 0.4 g of palladium-on-charcoal (10%) in 150 ml of methanol was hydrogenated at room temperature and normal pressure. After filtering off the catalyst the filtrate was concentrated and the residue was recrystallized from diethyl ether. There was obtained 0.35 g of (RS)-3-[5-(1,4-dioxa-spiro[4,5]decan-8-yl)-pyridin-2-yl]-5-methoxymethyl-oxazolidin-2-one. M.p.: 117°–121°.

EXAMPLE 23

(RS)-5-Methoxymethyl-3-[5-(4-oxo-cyclohexyl)-pyridin-2-yl]-oxazolidin-2-one

A solution of 0.5 g of (RS)-3-[5-(1,4-dioxa-spiro[4,5]decan-8-yl)-pyridin-2-yl]-5-methoxymethyl-oxazolidin-2-one in 20 ml of tetrahydrofuran and 5 ml of 2N hydrochloric acid was stirred at room temperature for 4 h. Then, 10 ml of 2N sodium hydroxide solution were added and the mixture was extracted several times with ethyl acetate. The organic phases were combined, dried with magnesium sulfate and concentrated. After chromatography with ethyl acetate on silica gel there was obtained 0.4 g of (RS)-5-methoxymethyl-3-[5-(4-oxo-cyclohexyl)-pyridin-2-yl]-oxazolidin-2-one. $^1$H-nmr (CDCl$_3$) ppm: 8.22 (s, 1H), 8.18 (d,1H), 7.58 (d, 1H), 4.78 (m,1H), 4.27 (t, 1H), 4.09 (t, 1H), 3.64 (m, 2H), 3.43 (s, 3H), 3.08 (m, 1H), 2.51 (m, 4H), 2.04 (bm, 4H).

EXAMPLE 24

(RS)-3-[5-(trans-4-Hydroxy-cyclohexyl)-pyridin-2-yl]-5-methoxymethyl-oxazolidin-2-one A solution of 0.4 g of (RS)-5-methoxymethyl-3-[5-(4-oxo-cyclohexyl)-pyridin-2-yl]-oxazolidin-2-one in 25 ml of methanol and 2.5 ml of water was treated with 0.2 g of sodium borohydride and stirred at room temperature for 16 h. Then, the mixture was concentrated and the residue was taken up in methylene chloride and washed with water. The aqueous phase was extracted with methylene chloride and the organic phases were combined, dried with magnesium sulfate and concentrated. The residue (0.4 g) was recrystallized from ethyl acetate and there was obtained 0.2 g of (RS)-3-[5-(trans-4-hydroxy-cyclohexyl)-pyridin-2-yl]-5-methoxymethyl-oxazolidin-2-one. M.p.: 142°–143°.

EXAMPLE 25

(RS)-3-[6-(1,4-Dioxa-spiro[4,5]decan-8-yl)-pyridin-3-yl]-5-methoxymethyl-oxazolidin-2-one A solution of 0.8 g of (RS)-3-[6-(1,4-dioxa-spiro[4,5]dec-7-en-8-yl)-pyridin-3-yl]-5-methoxymethyl-oxazolidin-2-one and 1.1 g of palladium-on-charcoal (10%) in 250 ml of methanol was hydrogenated at room temperature and normal pressure. After filtering off the catalyst the filtrate was concentrated. 1.2 g of (RS)-3-[6-(1,4-dioxa-spiro[4,5]decan-8-yl)-pyridin-3-yl]-5-methoxymethyl-oxazolidin-2-one were obtained. A sample was purified further on silica gel 60 with ethyl acetate as the eluent and boiled with diethyl ether. M.p.: 93°–94°.

EXAMPLE 26

(RS)-5-Methoxymethyl-3-[6-(4-oxo-cyclohexyl)-pyridin-3-yl]-oxazolidin-2-one

A solution of 0.8 g of (RS)-3-[6-(1,4-dioxa-spiro[4,5]decan-8-yl-pyridin-3-yl]-5-methoxymethyl-oxazolidin-2-one in 32 ml of tetrahydrofuran and 8 ml of 2N hydrochloric acid was stirred at room temperature for 4 h. Then, 15 ml of 2N sodium hydroxide solution were added and the mixture was extracted several times with ethyl acetate. The organic phases were combined, dried with magnesium sulfate and concentrated. There was obtained 0.7 g of (RS)-5-methoxymethyl-3-[6-(4-oxo-cyclohexyl)-pyridin-3-yl]-oxazolidin-2-one. $^1$H-nmr (CDCl$_3$) ppm: 8.49 (s, 1H), 8.19 (d, 1H), 7.23 (d, 1H), 4.81 (m, 1H), 4.09(t, 1H), 3.98 (t, 1H), 3.66 (m, 2H), 3.44 (s, 3H), 3.19 (m, 1H), 2.52 (m, 4H), 2.28 (m, 2H), 2.06 (m, 2H).

EXAMPLE 27

(RS)-3-[6-trans-(4-Hydroxy-cyclohexyl)-pyridin-3-yl]-oxazolidin-2-one

A solution of 0.7 g of (RS)-5-methoxymethyl-3-[6-(4-oxo-cyclohexyl)-pyridin-3-yl]-oxazolidin-2-one in 40 ml of methanol and 4 ml of water was treated with 0.3 g of sodium borohydride and stirred at room temperature for 16 h. Then, the mixture was concentrated and the residue was taken up in methylene chloride and washed with water. The aqueous phase was dried with magnesium sulfate and concentrated. The residue (0.4 g) was chromatographed over silica gel 60 with methylene chloride/methanol (50:1) and boiled with hexane. 0.2 g of (RS)-3-[6-trans-(4-hydroxy-cyclohexyl)-pyridin-3-yl]-oxazolidin-2-one was obtained. M.p.: 134°–136°.

EXAMPLE 28

(RS)-3-[(4-Cycloheptyl)phenyl]-5-methoxymethyl-oxazolidin-2-one 4.18 g (16.0 mmol) of ethyl 4-cycloheptylphenylcarbamate were treated with 1.3 g (16.0 mmol) of pyridine and 18 g (0.136 mol) of (RS)-4-methoxymethyl-1,3-dioxolan-2-one and stirred at 160° bath temperature for 20 hours. After cooling the reaction mixture was chromatographed on 400 g of silica gel 60 with ether. After recrystallization from isopropyl ether there were obtained 2.05 g of (RS)-3-[(4-cycloheptyl)phenyl]-5-methoxymethyl-oxazolidin-2-one as a white crystallizate. M.p.: 70°–72°.

EXAMPLE 29

(RS)-3-[(4-Adamantan-1-yl)phenyl]-5-methoxymethyl-oxazolidin-2-one 5.42 g (18.1 mmol) of ethyl 4-adamantan-1-yl-phenylcarbamate were treated with 1.43 g (18.1 mmol) of pyridine and 18.0 g (0.136 mol) of (RS)-4-methoxymethyl-1,3-dioxolan-2-one and stirred at 160° bath temperature for 20 hours. After cooling the reaction mixture was chromatographed on 500 g of silica gel 60 with ether. 1.4 g of (RS)-3-(4-adamantan-1-yl)phenyl]-5-methoxymethyl-oxazolidin-2-one were obtained as a white crystallizate after recrystallization from methylene chloride/ether. M.p.: 145°–147°.

EXAMPLE 30

(RS)-3-[trans-4-[4-(5-Methoxymethyl-2-oxo-Oxazolidin-3-yl)-phenyl]cyclohexyloxy]-propionitrile.

3.05 g (10.0 mmol) of (RS)-3-[4-trans-4-hydroxycyclohexyl)Phenyl]-5-methoxymethyl-oxazolidin-2-one were dissolved in 150 ml of methylene chloride and treated in succession with 0.64 g (12.0 mmol) of acrylonitrile and 1.35 g (12.0 mmol) of potassium tert-butylate. The reaction mixture was stirred at room temperature for 18 hours. Thereafter, it was washed with water and the organic phase was dried over sodium sulfate, filtered and evaporated. The residue (4.0 g) was chromatographed on 120 g of silica gel 60 with ethyl acetate/n-hexane (6:4). 1.8 g of (RS)-3-[trans-4-[4-(5-methoxymethyl-2-oxo-oxazolidin-3-yl)-phenyl]-cyclohexyloxy]-propionitrile were obtained after recrystallization from ethyl acetate. M.p.: 82°–84°.

EXAMPLE 31

(RS)-3-[trans-4-[4-(5-Methoxymethyl-2-oxo-oxazolidin-3-yl)-phenyl]cyclohexyloxy]propanamine HCl 545.3 mg (14.4 mmol) of sodium borohydride suspended in 20 ml of absolute tetrahydrofuran were treated at room temperature over 5 minutes with 1.64 g (14.4 mmol) of trifluoroacetic acid. Then, 1.29 g (3.6 mmol) of (RS)-3-[trans-4-[4-(5-methoxymethyl-2-oxo-oxazolidin-3-yl)-phenyl]-cyclohexyloxy]-propionitrile dissolved in 20 ml of absolute tetrahydrofuran were added dropwise thereto at room temperature within 15 minutes. After stirring for 18 hours the reaction mixture was evaporated, the residue was partitioned in water and methylene chloride, the organic phase was washed with water, dried over sodium sulfate, filtered and evaporated. The residue (1.4 g) was chromatographed on 39 g of silica gel 60 with methylene chloride (sat. NH$_3$)/methanol (98:2). The product in methylene chloride was washed with water, dried over sodium sulfate, filtered and the filtrate was made acid with ethereal hydrochloric acid. After recrystallization from methylene chloride/ether there were obtained 1.13 g of (RS)-3-[trans-4-[4-(5-methoxymethyl-2-oxo-oxazolidin-3-yl)-phenyl]cyclohexyloxy] propanamine HCl. M.p.: 173°–175°.

EXAMPLE 32

2-(4,5-Dihydro-oxazol-2-yl)-benzoic acid (RS)-trans-4-[4-(5-methoxymethyl-2-oxo-oxazolidin-3-yl)-phenyl]-cyclohexyl ester A solution of 4.58 g (15.0 mmol) of (RS)-3-[4-trans-4-hydroxy-cyclohexyl)-phenyl]-5-methoxymethyl-oxazolidin-2-one in 30 ml of absolute dimethylformamide was added dropwise under an argon atmosphere within 25 minutes to a suspension of 690 mg (15.8 mmol) of a 55% sodium hydride dispersion in 20 ml of absolute dimethylformamide and the mixture was stirred at room temperature for 3 hours. Subsequently, a solution of 3.81 g (15.0 mmol) of N-(2-bromoethyl)phthalimide in 20 ml of absolute dimethylformamide was added dropwise thereto and the mixture was stirred at room temperature overnight. Thereafter, the reaction mixture was treated with 0.9 g (15.0 mmol) of glacial acetic acid and evaporated. The residue was dissolved in ethyl acetate, washed with water, dried over sodium sulfate, filtered and evaporated. After recrystallization from ethyl acetate there were obtained 4.9 g of 2-(4,5-dihydro-oxazol-2-yl)-benzoic acid (RS)-trans-4-[4-(5-methoxymethyl-2-oxo-oxazolidin-3-yl)-phenyl]-cyclohexyl ester. M.p.: 182°–184°.

EXAMPLE 33

Acetic acid (RS)-trans-4-[4-(5-methoxymethyl-2-oxo-oxazolidin-3-yl)-phenyl]-cyclohexyl ester To a solution of 0.5 g (1.639 mmol) of (RS)-3-[4-trans-4-hydroxy-cyclohexyl)-phenyl]-5-methoxymethyl-oxazolidin-2-one in 20 ml of methylene chloride and 5 ml of pyridine was added dropwise while stirring a solution of 0.58 ml of acetyl chloride (8.195 mmol) in 10 ml of methylene chloride and the mixture was stirred at room temperature for a further 3 hours. The reaction mixture was poured into ice-water, made acid with 3N hydrochloric acid and extracted with methylene chloride. The organic phase was washed with water, dried over magnesium sulfate and the solvent was distilled off. The acetate crystallized upon treatment with t-butyl methyl ether. There was obtained 0.35 g (62%) of acetic acid (RS)-trans-4-[4-(5-methoxymethyl-2-oxo-oxazolidin-3-yl)-phenyl]-cyclohexyl ester. M.p.: 78°–79°.

EXAMPLE 34

Benzoic acid (RS)-trans-4-[4-(5-methoxymethyl-2-oxo-oxazolidin-3-yl)-phenyl]-cyclohexyl ester A solution of 0.5 g (1.639 mmol) of (RS)-3-[4-(trans-4-hydroxy-cyclohexyl)-phenyl]-5-methoxymethyl-oxazolidin-2-one in 20 ml of methylene chloride and 5 ml of pyridine was treated dropwise with a solution of 0.95 ml (8.195 mmol) of benzoyl chloride in 10 ml of methylene chloride and stirred at room temperature for a further 3 hours. The reaction mixture was poured into ice-water, made acid with 3N hydrochloric acid and extracted with methylene chloride. The organic phase was washed with wate, dried over magnesium sulfate and the solvent was distilled off. The benzoate crystallized upon treatment with t-butyl methyl ether. There was obtained 0.52 g (77%) of benzoic acid (RS)-trans-4-[4-(5-methoxymethyl-2-oxo-oxazolidin-3-yl)-phenyl]-cyclohexyl ester. M.p.: 104°–105°.

EXAMPLE 35

5-Methoxy-3-[4-[5-exo-[4-(5-methoxymethyl-2-oxo-oxazolidin-3-yl)-phenyl]-bicyclo[2.2.1]hept-2exo-yl]-phenyl]-oxazolidin-2-one The above-named compound is obtained as a byproduct in the preparation of the compound of Example 18 and can be separated by chromatography (silica gel, ethyl acetate/hexane (1:1)). M.p.: 152°–154°.

EXAMPLE 36

(RS)-4-Chloro-N-[2-[trans-4-(5-methoxymethyl-2-oxo-oxazolidin-3-yl)-phenyl]-cyclohexylamino]ethyl-benzamide hydrochloride A solution of 1.31 g (4.3 mmol) of (RS)-3-[4-(4-oxo-cyclohexyl)-phenyl]-5-methoxymethyl-oxazolidin-2-one, 2.0 g (10mmol) of N-(2-aminoethyl)-4-chlorobenzamide and 37 mg (0.2 mmol) of p-toluenesulfonic acid monohydrate in 20 ml of toluene and 6 ml of dimethylformamide was boiled on a water separator for 7 hours. While stirring there were added at room temperature 330 mg (8.7 mmol) of sodium borohydride and, after 30 minutes, 10 ml of 1N hydrochloric acid. The organic phase was separated. The aqueous phase was extracted twice with methylene chloride. Then, the organic phases were dried with sodium sulfate, concentrated and chromatographed over silica gel with methylene chloride/methanol (9:1). The solid obtained was recrystallized from ethanol/ether. 200 mg of white crystals were obtained. M.p.: 233°–235°.

EXAMPLE 37

(RS)-5-Methoxymethyl-3-[4-(4-methylene-cyclohexyl)-phenyl]-oxazolidin-2-one 5.76 g (13.8mmol) of methyltriphenylphosphonium bromide/sodium amide mixture were stirred at room temperature under argon in 170 ml of tetrahydrofuran for 1 hour. Then, a solution of 4.20 g (13.8 mmol) of (RS)-3-[4-(4-oxo-cyclohexyl)-phenyl]-5-methoxymethyl-oxazolidin-2-one was added dropwise within 5 minutes. After boiling under reflux overnight the mixture was poured into water and extracted with methylene chloride. After drying with sodium sulfate and concentrating the residue was chromatographed over silica gel with ethyl acetate/n-hexane (1:2). 3.47 g (83%) of a solid were obtained. A small sample was recrystallized from hexane. M.p.: 63°–65°.

EXAMPLE 38

(RS)-3-[4-(Cis- and trans-4-Hydroxymethyl-cyclohexyl)-phenyl]-5-methoxymethyl-oxazolidin-2-one 0.19 g (5.0 mmol) of sodium borohydride was added to a suspension of 1.50 g (5.0mmol) of (RS)-methoxymethyl-3-[4-(4-methylencyclohexyl)-phenyl]-oxazolidin-2-one in 250 ml of tetrahydrofuran and 0.46 ml (5.0 mmol) of dimethyl sulfate was added dropwise thereto. After stirring at about 40° for 4 hours the mixture was cooled to 5° and 1.5 ml of 2N sodium hydroxide solution were added. Thereafter, 0.77 ml of 30% $H_2O_2$ (7.5 mmol) was slowly added dropwise. The mixture was poured into 100 ml of saturated sodium chloride solution, the organic phase was separated and the aqueous phase was extracted with methylene chloride. The organic phases were dried with sodium sulfate, concentrated and chromatographed over silica gel with methylene chloride/methanol. 350 mg of a colorless oil were obtained. MS: m/e (% basic peak): 319 (M+, 73), 246 (16), 233 (16), 170 (30), 158 (16), 144 (86), 118 (60), 95 (19), 91 (25), 77 (24), 71 (60), 45 (100).

EXAMPLE 39

(RS)-3-[4-(cis or trans-4-Hydroxy-4-methyl-cyclohexyl)-phenyl]-5-methoxymethyl-oxazolidin-2-one A solution of 525 mg (1.6 mmol) of mercuric acetate in 10 ml of water was treated with 10 ml of tetrahydrofuran. After stirring for 15 minutes a solution of 500 mg (1.7 mmol) of (RS)-5-methoxymethyl-3-[4-(4-methylenecyclohexyl)-phenyl]-oxazolidin-2-one in 10 ml of tetrahydrofuran was added dropwise to this suspension. The mixture was stirred at room temperature for 1.5 hours. Then, 10 ml of 2N sodium hydroxide solution were added and, after stirring for 10 minutes, a solution of 200 ml (5.3 mmol) of sodium borohydride in 10 ml of 2N sodium hydroxide solution was added. After stirring for 30 minutes the mixture was extracted with methylene chloride and the organic phase was washed with saturated sodium chloride solution and dried with sodium sulfate. After distilling off the solvent the residue was chromatographed over silica gel with ethyl acetate/hexane (1:2). 150 mg of white crystals were obtained. M.p.: 118°–119°.

EXAMPLE 40

(RS)-3-[4-(1,4-Dioxa-spiro[4,5]dec-8-yl)-phenyl]-5-methoxymethyl]-oxazolidin-2-one A solution of 0.60 g (2 mmol) of (RS)-3-[4-(4-oxo-cyclohexyl)phenyl]-5-methoxymethyl-oxazolidinone, 0.15 g (2.4 mmol) of ethylene glycol and 30 mg of p-toluenesulfonic acid monohydrate in 20 ml of toluene was boiled on a water separator for 7 hours. The toluene was filtered off and the residue was suspended in 10 ml of 2N sodium hydroxide solution and extracted with methylene chloride. After drying with sodium sulfate the solvent was distilled off. Chromatography over silica gel with ether and recrystallization with ether gave 0.4 g of white crystals. M.p.: 120°–123°.

EXAMPLE 41

(RS)-3-[4-(cis-4-Fluoro-cyclohexyl)-phenyl]-5-methoxymethyl-oxazolidin-2-one 0.5 g of (RS)3-[4-(trans-4-hydroxy-cyclohexyl)-phenyl]-5-methoxymethyl-oxazolidin-2-one was dissolved in 10 ml of methylene chloride and treated at room temperature within 30 minutes with a mixture of 2.2 ml of diethylaminosulfur trifluoride and 5 ml of methylene chloride. After stirring at room temperature for 2 hours the mixture was poured into 50 ml of ice-water and extracted twice with methylene chloride. The organic phase was washed with sodium chloride solution, sodium hydrogen carbonate solution and again with a sodium chloride solution, dried with magnesium sulfate and concentrated. The residue, 0.6 g of yellow honey, was chromatographed on a 30-fold amount of silica gel with methylene chloride-ethyl acetate (19:1) and yielded 80 mg of (RS)-3-[4-(cis-4-fluoro-cyclohexyl)-phenyl]-5-methoxymethyl-oxazolidin-2-one as a colorless oil. $^1$H-NMR (CDCl$_3$)ppm: 7.47 (d,2H), 7.24 (d,2H), 4.88 (bd, 1H), 4.74 (m,1H), 4.04 (t, 1H), 3.91 (m,1H), 3.64 (d,2H), 3.43 (s,3H), 2.53 (m,1H), 2.16 (m,2H), 1.72 (m,6H).

EXAMPLE 42

(RS)-3-[4-(trans-4-Amino-cyclohexyl)-phenyl]-5-methoxymethyl-oxazolidin-2-one hydrochloride (1:1)

a) A mixture of 1.0 g of (R,S)-3-[4-(4-oxo-cyclohexyl)-phenyl]-5-methoxymethyl-oxazolidin-2-one, 0.1 g of p-toluenesulfonic acid and 0.43 ml of benzylamine in 100 ml of toluene was boiled on a water separator for 3 hours. The solvent was removed and the residue was dissolved in 50 ml of methanol and stirred at room temperature overnight with 150 mg of sodium borohydride. The solvent was removed and the residue was treated with 1N hydrochloric acid and washed with ethyl acetate. The aqueous phase was made basic with sodium hydroxide solution and extracted with methylene chloride. The methylene chloride phase was dried with magnesium sulfate and concentrated. Crystallization of the residue from ethyl acetate/hexane yielded 0.6 g of beige colored crystals of a mixture of (RS)-3-[4-(cis- and (RS)-3-[4-(trans-benzyl-amino-cyclohexyl)-phenyl]-5-methoxymethyl-oxazolidin-2-one. M.p.: 93°–94°.

b) 0.5 g of the mixture of (RS)-3-[4-(cis- and (RS)-3-[4-(trans-benzyl-amino-cyclohexyl)-phenyl]-5-methoxymethyl-oxazolidin-2-one was dissolved in 50 ml of ethanol with the addition of one equivalent of 1N hydrochloric acid and hydrogenated with palladium/charcoal (10%) as the catalyst at room temperature and normal pressure. After adding diethyl ether 0.3 g of (RS)-3-[4-(trans-4-amino-cyclohexyl)-phenyl]-5-methoxymethyl-oxazolidin-2-one-hydrochloride (1:1) separated as colorless crystals. M.p.: >250°. $^1$H-NMR (DMSO) ppm: 8.12 (bs,3H), 7.47 (d,2H), 7.25 (d,2H), 4.81 (m,1H), 4.09 (t,1H), 3.77 (m,1H), 3.58 (m,2H), 3.32 (s,3H), 3.03 (m,1H), 2.47 (m,1H), 2.06 (m,2H), 1.80 (m,2H), 1.50 (m,4H).

EXAMPLE 43

(R,S)-3-[4-(trans-4-Benzhydryloxy-cyclohexyl)-phenyl]-5-methoxymethyl-oxazolidin-2-one 0.5 g of (RS)-3-[4-(trans-4-hydroxy-cyclohexyl)-phenyl]-5-methoxymethyl-oxazolidin-2-one in 5 ml of ethyldiisopropylamine was heated with 0.35 ml of chlorodiphenylmethane to 100° and stirred at this temperature for 7 hours. The reaction mixture was cooled, acidified with 1N hydrochloric acid and extracted with ethyl acetate. The organic phase was washed neutral with water, dried with magnesium sulfate and concentrated. The residue (0.7 g) was chromatographed on a 30-fold amount of silica gel with methylene chloride/ethyl acetate mixtures. 0.3 g of (RS)-3-[4-(trans-4-benzhydryloxy-cyclohexyl)-phenyl]-5-methoxymethyl-oxazolidin-2-one was obtained as colorless crystals. M.p.: 146°–148°.

EXAMPLE 44

9:1 Mixture of (RS)-3-[4-(trans- and cis-4-benzyloxy-cyclohexyl)-phenyl]-5-methoxymethyl-oxazolidin-2-one 1.0 g of (RS)-3-[4-(hydroxy-cyclohexyl)-phenyl]-5-methoxymethyl-oxazolidin-2-one in 10 ml of dimethylformamide was treated with 0.21 g of sodium hydride and 0.78 ml of benzyl bromide. The reaction mixture was stirred at room temperature overnight. After adding 50 ml of ethyl acetate the mixture was washed three times with water. The aqueous phases were extracted with ethyl acetate. The organic phases were combined, dried with magnesium sulfate and concentrated. Chromatography of the residue (1.6 g) on a 30-fold amount of silica gel with methylene chloride/ethyl acetate mixtures yielded 0.8 g of yellow oil which crystallized from tert-butyl methyl ether. 0.6 g of a 9:1 mixture of (RS)-3-[4-(trans- and cis-4-benzyloxy-cyclohexyl)-phenyl]-5-methoxymethyl-oxazolidin-2-one was obtained as colorless crystals. M.p.: 82°–84°. $^1$H-NMR (CDCl$_3$) ppm: 7.46 (d,2H), 7.35 (m,5H), 7.23 (d,2H), 4.74 (m,1H), 4.60 (s,2H), 3.99 (t,1H), 3.90 (m,1H), 3.63 (d,2H), 3.43 (s,3H), 3.40 (m,1H), 2.50 (m,1H), 2.22 (m,2H), 1.91 (m,2H), 1.46 (m,4H).

EXAMPLE 45

(R)-3-[4-(trans-4-Methoxy-cyclohexyl)-phenyl]-5-methoxymethyl-oxazolidin-2-one 1.4 g of (R)-3-[4-(trans-4-hydroxy-cyclohexyl)-phenyl]-5-methoxymethyl-oxazolidin-2-one in 14 ml of dimethylformamide were treated with 0.3 g of sodium hydride and 1.43 ml of methyl iodide. The reaction mixture was stirred at 40° overnight. After adding 100 ml of diethyl ether the mixture was washed three times with water. The aqueous phases were extracted with diethyl ether. The organic phases were combined, dried with magnesium sulfate and concentrated. Chromatography of the residue (1.5 g) on a 30-fold amount of silica gel with methylene chloride/ethyl acetate mixtures yielded 1.3 g of colorless oil which crystallized from tert-butyl methyl ether. 1.1 g of (R)-3-[4-(trans-4-methoxy-cyclohexyl)-phenyl]-5-methoxymethyl-oxazolidin-2-one were obtained as colorless crystals. M.p.: 73°–74°.

EXAMPLE 46

(RS)-3-(4-Cyclohex-1-enyl-phenyl)-5-methoxymethyl-oxazolidin-2-one

A solution of 410 mg of bis-(triphenylphosphine)-palladium(II) diacetate, 2.0 g of (RS)-3-(4-iodophenyl)-5-methoxymethyl-oxazolidin-2-one and 1.8ml of 1-tributyl-stannyl-1-cyclohexene in 10 ml of dimethylformamide was stirred at 80° for 18 hours. The reaction mixture was poured into 100 ml of water and extracted three times with ethyl acetate. The organic phase was washed with saturated potassium fluoride solution, saturated sodium chloride solution and water, dried with magnesium sulfate and concentrated. Chromatography of the residue (2.0 g) on a 30-fold amount of silica gel with ethyl acetate/hexane (1:2) yielded 0.7 g of solid which crystallized from ethyl acetate/hexane. 0.3 g of (RS)-3-(4-cyclohex-1-enyl-phenyl)-5-methoxymethyl-oxazolidin-2-one was obtained as colorless crystals. M.p.: 106°–108°.

EXAMPLE 47

Mixture of (RS)- and (SR)-3-[(RS)-4-cyclohex-3-enyl-phenyl]-5-methoxymethyl-oxazolidin-2-one A solution of 2.0 g of (RS)-3-[4-(hydroxy-cyclohexyl)-phenyl]-5-methoxymethyl-oxazolidin-2-one, 2.1 g of triphenylphosphine and 1.8 g of benzoic acid in 80 ml of tetrahydrofuran was treated at room temperature within 15 minutes with 1.2 ml of diethyl azodicarboxylate in 20 ml of tetrahydrofuran and stirred at room temperature for 22 hours. The reaction mixture was concentrated and the residue was dissolved in 100 ml of ethyl acetate, washed twice with 10% sodium carbonate solution and twice with saturated sodium chloride solution, dried with magnesium sulfate and concentrated. Chromatography of the residue (7.0 g) on a 30-fold amount of silica gel with methylene chloride/hexane mixtures yielded as a byproduct 0.6 g of oil which crystallized from ethyl acetate/hexane. 0.4 g of a mixture of (RS)- and (SR)-3-[(RS)-4-cyclohex-3-enyl-phenyl]-5-methoxymethyl-oxazolidin-2-one was obtained as colorless crystals. M.p.: 74°–75°. $^1$H-NMR (CDCl$_3$ ppm: 7.48 (d,2H), 7.23 (d,2H), 5.75 (m,2H), 4.75 (m,1H), 4.04 (t, 1H), 3.91 (m,1H), 3.64 (d,2H), 3.43 (s,3H), 2.78 (m,1H), 2.16 (m,4H), 1.88 (m,1H), 1.75 (m,1H).

EXAMPLE 48

A mixture of (RS)- and (SR)-[4-[4-[(RS)-5-methoxymethyl-2-oxo-oxazolidin-3-yl]-phenyl]-cyclohexylidene]-acetonitrile 0.46 g of sodium was dissolved in 50 ml of ethanol under argon. Thereafter, 3.5 g (=3.1 ml) of diethyl cyanomethylphosphonate dissolved in 10 ml of ethanol were added at 20°. The mixture was stirred at room temperature for a further 30 minutes and then 2.0 g of (RS)-5-methoxymethyl-3-[4-(4-oxo-cyclohexyl)-phenyl]-oxazolidin-2-one were added. Thereafter, the mixture was stirred at reflux for a further 1 hour, cooled to room temperature, adjusted to pH 6 with about 0.7 ml of glacial acetic acid and evaporated in a vacuum. The crude mixture (~4.2 g) was chromatographed through 200 g of silica gel. Elution with dichloromethane/ethyl acetate 9:1 gave 1.65 g of a mixture of (RS)- and (SR)-[4-[4-[(RS)-5-methoxymethyl-2-oxo-oxazolidin-3-yl]-phenyl]-cyclohexylidene]-acetonitrile as white crystals. A sample recrystallized from ethyl acetate/hexane gave white crystals of m.p. 121°–125°.

EXAMPLE 49

(RS)-[trans-4-[4-(5-Methoxymethyl-2-oxo-oxazolidin-3-yl)-phenyl]-cyclohexyl]-acetonitrile 1.65 g of a mixture of a) (R)-[4-[4-[(R)-, b) (R)-[4-[4-[(S)-, c)(S)-[4-[4-[(R)- and d) (S)-[4-[4-[(S)-5-methoxymethyl-2-oxo-oxazolidin-3-yl]-phenyl]-cyclohexylidene]-acetonitrile (ratio a:b=c:d=1:1) were hydrogenated in 175 ml of glacial acetic acid and 0.3 g of 10% Pd-charcoal at normal pressure and room temperature until the theoretical uptake had taken place (~16 hours). The catalyst was filtered off under suction and the filtrate was evaporated in a vacuum. The residue (1.6 g) was dissolved in ethyl acetate and washed with 10% sodium hydrogen carbonate solution and with saturated sodium chloride solution. After drying and evaporation there were obtained 1.6 g of crystals which, for purification, were chromatographed over 30 g of silica gel. Elution was carried out with dichloromethane/ethyl acetate 9:1. After pooling the fractions which were pure according to thin-layer chromatography and crystallization from ethyl acetate/hexane 0.72 g of (RS)-[trans-4-[4-(5-methoxymethyl-2-oxo-oxazolidin-3-yl)-phenyl]-cyclohexyl]-acetonitrile was obtained as white crystals of m.p. 118°–120°.

EXAMPLE 50

Mixture of (RR) and
(SR)-4-[4-(5-Methoxymethyl-2-oxo-oxazolidin-3-
yl)-phenyl]-cyclohexyl]-acetonitrile 1.1 g of (R)-[4-[4-(5-methoxymethyl-2-oxo-oxazolidin-3-yl]-phenyl]-cyclohexylidene]-acetonitrile were dissolved in 50 ml of methanol, treated with 0.2 g of 10% Pd-charcoal and hydrogenated at room temperature at normal pressure until the theoretical hydrogen uptake had taken place. The catalyst was filtered off under suction and the filtrate was evaporated in a vacuum. The oily residue was chromatographed over 15 g of silica gel. Elution was carried out with dichloromethane/ethyl acetate 9:1. The fractions which were pure according to thin-layer chromatography were pooled and crystallized from ethyl acetate/hexane. 0.64 g of (R)-[trans-[4-[4-(5-methoxymethyl-2-oxo-oxazolidin-3-yl)-phenyl]-cyclohexyl]-acetonitrile was obtained as white crystals of m.p. 90°–91°.

$$[\alpha]_D^{20°} 589 = -39.6°$$
$$[\alpha]_{Hg}^{546} = -47.6°$$
$(c = 1\% \text{ in dichloromethane})$

EXAMPLE 51

1:1 mixture of cis- and
trans-(RS)-3-[4-[4-(2-amino-ethyl)-
cyclohexyl]-phenyl]-5-methoxymethyl-oxazolidin-2-one
hydrochloride (1:1)

2.1 g of a mixture of a) (R)-[4-[4-[(R)-, b) (R)-[4-[4-[(S)-, c)(S)-[4-[4-[(R)- and d) (S)-[4-[4-[(S)-5-methoxymethyl-2-oxo-oxazolidin-3-yl]-phenyl]-cyclohexylidene]-acetonitrile (ratio a:b=c:d=1:1) were hydrogenated in 200 ml of 20% (wt./vol.) methanolic ammonia and 3.0 g of Raney-nickel for about 40 hours at normal pressure and room temperature until the theoretical hydrogen uptake had taken place. The catalyst was filtered off under suction and the filtrate was evaporated in a vacuum. The crude residue (~1.8 g) was chromatographed through 15 g of silica gel. Elution was carried out with dichloromethane/methanol/25% ammonia (250:5:1) and with dichloromethane saturated with 25% ammonia+5% methanol. The fractions which were pure according to thin-layer chromatography were pooled and evaporated. 1.4 g of base were obtained as a turbid oil. 0.7 g of this was converted into the hydrochloride (ethanolic hydrochloric acid/ether). 0.5 g (1:1) of a mixture of cis- and trans-(RS)-3-[4-[4-(2-amino-ethyl)-cyclohexyl]-phenyl]-5-methoxymethyl-oxazolidin-2-one hydrochloride (1/1) was obtained as white crystals of m.p. 203°–207°.

EXAMPLE 52

(RS)-N-[2-[4-[4-(5-Methoxymethyl-2-oxo-
oxazolidin-3-yl)-phenyl]-cyclohexyl]-ethyl]-acetamide
(trans:cis mixture=6:1)

0.57 g of a 1:1 mixture of cis- and trans-(RS)-3-[4-[4-(2-aminoethyl)-cyclohexyl]-phenyl]-5-methoxymethyl-oxazolidin-2-one was dissolved in 2 ml of pyridine and treated with 0.21 g of acetic anhydride. The reaction mixture was stirred at room temperature for 3.5 hours and thereafter dissolved in dichloromethane. The organic phase was washed with 1N hydrochloric acid, water, sodium hydrogen carbonate and saturated sodium chloride solution, subsequently dried and evaporated. 0.75 g of turbid oil remained as the residue and this was crystallized from ethyl acetate/methyl tert.butyl ether. 0.25 g of (RS)-N-[2-[4-[4-(5-methoxymethyl-2-oxo-oxazolidin-3-yl)-phenyl]-cyclohexyl]ethyl]-acetamide (trans:cis mixture=6:1) was obtained as white crystals of m.p. 120°–122°.

EXAMPLE 53 t-Butyl
(RS)-4-[4-(5-Methoxymethyl-2-oxo-oxazolidin-3-
yl)-phenyl]-piperidine-1-carboxylate 5.5 g (15.0 mmol) of t-butyl 4-(4-ethoxycarbonylamino-phenyl)-piperidine-1-carboxylate and 20 g (0.15 mol) of (RS)-4-(methoxymethyl)-1,3-dioxolan-2-one were stirred intensively in the presence of 2.37 g of pyridine for 18 hours at an oil bath temperature of 160°. After cooling the reaction mixture it was chromatographed on 840 g of silica gel 60 with ether. 3.4 g of t-butyl (RS)-4-[4-(5-methoxymethyl-2-oxo-oxazolidin-3-yl)-phenyl]-piperidine-1-carboxylate were obtained as a yellowish oil. $^1$H-NMR (CDCl$_3$) ppm: 7.48 (d,2H), 7.22 (d,2H), 4.76 (m,1H), 4.25 (bd,2H), 4.05 (t,1H), 3.92 (t,1H), 3.64 (d,2H), 3.43 (s,3H), 2.80 (t,2H), 2.64 (m,1H), 1.78 (bd,2H), 1.61 (m,2H), 1.49 (s,9H).

EXAMPLE 54

(RS)-4-[4-(5-Methoxymethyl-2-oxo-oxazolidin-3-yl)-
phenyl]-piperidine.HCl 2.51 g (6.4 mmol) of t-butyl (RS)-4-[4-(5-methoxymethyl-2-oxo-oxazolidin-3-yl)-phenyl]-piperidin-1-carboxylate were dissolved in 40 ml of ethyl acetate and treated while stirring at room temperature with 40 ml of a 2.2 molar, HCl-saturated ethyl acetate solution. After 90 minutes the suspension was evaporated and the residue was distilled with toluene. There were obtained 1.47 g of (RS)-4-[4-(5-methoxymethyl-2-oxo-oxazolidin-3-yl)-phenyl]-piperidine.HCl. M.p.: 161°–163°. $^1$H-NMR (DMSO) ppm: 8.98 (bs, 2H), 7.52 (d,2H), 7.24 (d,2H), 4.81 (m,1H), 4.10 (t, 1H), 3.79 (t,1H), 3.58 (m,2H), 3.35 (m,2H), 3.32 (s,3H), 2.97 (bm,2H), 2.80 (m,1H), 1.87 (bm,4H).

EXAMPLE 55

(RS)-1-Benzyl-4-[4-(5-methoxymethyl-2-oxo-
oxazolidin-3-yl)-phenyl]-piperidine.HCl 290.4 mg (1.0 mmol) of (RS)-4-[4-(5-methoxymethyl-2-oxo-oxazolidin-3-yl)-phenyl]-piperidine were dissolved in 5 ml of abs. dimethylformamide and treated with 171.0 mg(1.0 mmol) of benzyl bromide in the presence of 404.8 mg (4.0 mmol) of triethylamine. The reaction mixture was stirred at 600 for 90 minutes. Thereafter, it was evaporated, the residue was partitioned in ethyl acetate and 3N ammonia solution and the organic phase was washed with water, dried over sodium sulfate, filtered and evaporated. The base was dissolved in ethanol, made acid with ethereal hydrochloric acid and distilled repeatedly with toluene. After recrystallization from ethanol/ether there were obtained 291.2 mg of (RS)-1-benzyl-4-[4-(5-methoxymethyl-2-oxo-oxazolidin-3-yl)-phenyl]-piperidine.HCl. M.p.: 175°–177°.

EXAMPLE 56

(RS)-1-(4-Fluorobutyrophenon-ω-yl)-4-[4-(5-methoxymethyl-2-oxo-oxazolidin-3-yl)-phenyl]-piperidine.HCl 253.0 mg (0.87 mmol) of (RS)-4-[4-(5-methoxymethyl-2-oxo-oxazolidin-3-yl)-phenyl]-piperidine were dissolved in 15 ml of abs. dimethylformamide and treated with 174.8 mg (0.87 mmol) of ω-chloro-4-fluorobutyrophenone in the presence of 352.7 mg (3.485 mmol) of triethylamine. The reaction mixture was stirred at 100° for 5 hours. Thereafter, it was evaporated, the residue was partitioned in ethyl acetate and 3N ammonia solution and the organic phase was washed with water, dried over sodium sulfate, filtered and evaporated. The residue was dissolved in ethanol and made acid with ethereal hydrochloric acid. After recrystallization from alcohol/ether there were obtained 135.9 mg of (RS)-1-(4-fluorobutyrophenon-w-yl)-4-[4-(5-methoxymethyl-2-oxo-oxazolidin-3-yl)-phenyl]-piperidine. HCl. M.p.: 182°–184°.

EXAMPLE 57

(RS)-4-[4-(5-Methoxymethyl-2-oxo-oxazolidin-3-yl)-phenyl]-1-(4-trifluoromethyl-benzoyl)-piperidine 273.1 mg (0.94 mmol) of (RS)-4-[4-(5-methoxymethyl-2-oxo-oxazolidin-3-yl)-phenyl]-piperidine. HCl were dissolved in 20 ml of methylene chloride and treated with 196.2 mg (0.94 mmol) of 4-trifluoromethylbenzoyl chloride in the presence of 380.7 mg (3.76 mmol) of triethylamine. The reaction mixture was stirred at room temperature for 17 hours. Thereafter, it was treated with ethyl acetate, washed with 1N hydrochloric acid and water and dried over sodium sulfate. After recrystallization from ethyl acetate/ether there were obtained 356.3 mg of (RS)-4-[4-(5-methoxymethyl-2-oxo-oxazolidin-3-yl)-phenyl]-1-(4-trifluoromethyl-benzoyl)-piperidine. M.p. 164°–166°.

EXAMPLE 58

(RS)-1-Acetyl-4-[4-(5-methoxymethyl-2-oxo-oxazolidin-3-yl)-phenyl]-piperidine 177.1 mg (0.61 mmol) of (RS)-4-[4-(5-methoxymethyl-2-oxo-oxazolidin-3-yl)-phenyl]-piperidine were dissolved in 20 ml of methylene chloride and treated with 68.5 mg (0.67 mmol) of acetic anhydride in the presence of 53.1 mg (0.67 mmol) of pyridine. After stirring at room temperature for 18 hours the mixture was washed with water and the organic phase was dried over sodium sulfate. After filtration and evaporation of the filtrate the product was dried in a high vacuum. 197.3 mg of (RS)-1-acetyl-4-[4-(5-methoxymethyl-2-oxo-oxazolidin-3-yl)-phenyl]-piperidine were obtained as a yellowish oil. $^1$H-NMR (CDCl$_3$) ppm: 7.49 (d,2H), 7.20 (d,2H), 4.80 (m,2H), 4.05 (t, 1H), 3.92 (m,2H), 3.64 (d,2H), 3.43 (s,3H), 3.21 (m,1H), 2.68 (m,2H), 2.14 (s,3H), 1.85 (m,2H), 1.60 (m,2H).

EXAMPLE 59

(RS)-4-[4-(5-Methoxymethyl-2-oxo-oxazolidin-3-yl)-phenyl]-1-(1-oxo-3-phenyl-2,(E)-propenyl)-piperidine 201.7 mg (0.695 mmol) of (RS)-4-[4-(5-methoxymethyl-2-oxo-oxazolidin-3-yl)-phenyl]-piperidine.HCl were dissolved in 15 ml of methylene chloride and treated dropwise with a solution of 115.7 mg (0.695 mmol) of cinnamyl chloride in 5 ml of methylene chloride in the presence of 281.2 mg (2.78 mmol) of triethylamine while stirring at room temperature. After 17 hours the mixture was diluted with ethyl acetate and the organic phase was washed with 1N hydrochloric acid and water. After recrystallization from ethyl acetate/ether there were obtained 228.9 mg of (RS)-4-[4-(5-methoxymethyl-2-oxo-oxazolidin-3-yl)-phenyl]-1-(1-oxo-3-phenyl-2-(E)-propenyl)-piperidine. M.p.: 136°–138°.

EXAMPLE 60

(RS)-4-[4-(5-Methoxymethyl-2-oxo-oxazolidin-3-yl)-phenyl]-piperidine-1-carboxylate 1.12 g (3.5 mmol) of ethyl 4-(4-ethoxycarbonylamino-phenyl)-piperidine-1-carboxylate were treated with 4.0 g (30.28 mmol) of (RS)-4-(methoxymethyl)-1,3-dioxolan-2-one in the presence of 276.8 mg (3.5 mmol) of pyridine and stirred intensively for 18 hours at an oil bath temperature of 160°. After cooling the reaction mixture was chromatographed on 125 g of silica gel 60 with ether. After recrystallization from methylene chloride/isopropyl ether there were obtained 976 mg of ethyl (RS)-4-[4-(5-methoxymethyl-2-oxo-oxazolidin-3-yl)-phenyl]-piperidine-1-carboxylate. M.p.: 86°–88°.

EXAMPLE 61

(R)-5-Methoxymethyl-3-[4-(trans-4-methylsulfanylmethoxy-cyclohexyl)-phenyl]-oxazolidin-2-one 9.5 g (31.11 mmol) of (R)-3-[trans-(4-hydroxycyclohexyl)-phenyl]-5-methoxymethyl-oxazolidin-2-one were dissolved in 120 ml of dimethyl sulfoxide and treated in succession with 2 ml of water, 25 ml of glacial acetic acid and 80 ml of acetic anhydride. The reaction mixture was stirred at room temperature for 22 hours. Thereafter, it was introduced portionwise into an ice-cooled solution of 130 g of sodium carbonate in 2l of water. After the addition the mixture was stirred for a further 1 hour. Thereafter, the product was extracted with methylene chloride and the organic phase was washed with water, dried over sodium sulfate, filtered and evaporated. There were obtained 11.2 g of yellowish oil which, upon treatment with ether/n-hexane, gave crystalline (R)-5-methoxymethyl-3-[4-(trans-4-methylsulfanylmethoxy-cyclohexyl)-phenyl]-oxazolidin-2-one. M.p.: 54°–56°, $[\alpha]_D$=−30.8° (c=1.0, CHCl$_3$). $^1$H-NMR (CDCl$_3$) ppm: 7.47 (d,2H), 7.21 (d,2H), 4.70 (m,1H), 4.04 (t, 1H), 3.93 (t,1H), 3.70 (m,1H), 3.63 (d,2H), 3.43 (s,3H), 2.50 (m,1H), 2.18 (s,3H), 2.12 (d,2H), 1.90 (d,2H), 1.56 (bm,4H).

EXAMPLE 62

(R)-3-[4-(trans-4-Methanesulfinylmethoxy-cyclohexyl)-phenyl]-5-methoxymethyl-oxazolidin-2-one (S-oxide R:S=1:1, diastereomer mixture)

10.7 g (29.28 mmol) of (R)-5-methoxymethyl-3-[4-(trans-4-methylsulfanylmethoxy-cyclohexyl)-phenyl]-oxazolidin-2-one were dissolved in 500 ml of methanol, cooled to 0° and treated dropwise while stirring during 90 minutes with a solution of 4.7 g (22.0 mmol) of sodium periodate in 150 ml of water. The reaction mixture was stirred in a cold storage chamber at 4°–5° for 19 hours. Thereafter, it was diluted with 1 l of water and extracted with methylene chloride. The organic phase was washed with water, dried over sodium sulfate and filtered. The filtrate was filtered through a 400 g silica gel 60 pad and washed in succession and separately with ethyl acetate (800 ml), methanol (1 l) and tetrahydrofuran (800 ml). 3.16 g of educt remained behind after evaporation of the ethyl acetate eluate. After evaporation the methanol and tetrahydrofuran eluates gave 8.11 g of (R)-3-[4-(trans-4-methanesulfinylmethoxy-cyclohexyl)-phenyl]-5-methoxymethyl-oxazolidin-2-one (S-oxide R:S=1:1 diastereomer mixture) as a yellow oil, b.p. 205°/0.02 mbar, $[\alpha]_D$=−32.2° (c=1.0%, DMSO).

EXAMPLE 63

(R)-[trans-4-[4-(5-Methoxymethyl-2-oxo-oxazolidin-3-yl)-phenyl]-cyclohexyloxy]-acetonitrile 7.7 g (20.2 mmol) of (R)-3-[4-(trans-4-methanesulfinyl-methoxy-cyclohexyl)-phenyl]-5-methoxymethyl-oxazolidin-2-one (S-oxide, RS=1:1 diastereomer mixture) were dissolved in 200 ml of abs. tetrahydrofuran and treated dropwise while stirring during 30 minutes with a solution of 17.73 g (0.179 mol) of trimethylsilyl chloride in 40 ml of abs. tetrahydrofuran in the presence of 420 mg (1.32 mmol) of zinc iodide. The reaction mixture was stirred at room temperature for 24 hours. Thereafter, it was evaporated, the residue was partitioned in ethyl acetate-water and the organic phase was washed with water, dried over sodium sulfate, filtered and evaporated. The residue (7.75 g) was chromatographed on 320 g of silica gel 60 with ethyl acetate/n-hexane (1:1). There were obtained 2.64 g of (R)-[trans-4-[4-(5-methoxymethyl-2-oxo-oxazolidin-3-yl)-phenyl]-cyclohexyloxy]-acetonitrile as a colorless oil; b.p.: 210°/0.02 mbar; $[\alpha]_D$=−32.2° (c=1.0% in CHCl$_3$). $^1$H-NMR (CDCl$_3$) ppm: 7.48 (d,2H), 7.20 (d,2H), 4.75 (m,1H), 4.32 (d,2H), 4.02 (t,1H), 3.93 (t,1H), 3.64 (d,2H), 3.61 (m,1H), 3.43 (s,3H), 2.55 (m,1H), 2.39 (m,2H), 1.95 (m,2H), 1.50 (bm,4H). After recrystallization from ether/hexane there were obtained white cristalls. M.p.: 43°–45° C.

EXAMPLE 64

(RS)-5-Methoxymethyl-3-[4-(trans-4-methylsulfanylmethoxy-cyclohexyl)-phenyl]-oxazolidin-2-one 305.4 mg (1.0 mmol) of (RS)-3-[trans-4-hydroxycyclohexyl)-phenyl]-5-methoxymethyl-oxazolidin-2-one were placed in 35 ml of cyclohexane and treated at room temperature while stirring with 186.9 mg (1.1 mmol) of silver nitrate, 121.4 mg (1.2 mmol) of triethylamine and 115.9 mg (1.2 mmol) of chloromethyl methyl sulfide. The reaction mixture was stirred for 20 hours. Thereafter, silver chloride was filtered off over Dicalit, the filtrate was washed with saturated sodium hydrogen carbonate and the organic phase was dried over sodium sulfate, filtered and evaporated. 354.5 mg of (RS)-5-methoxymethyl-3-[4-(trans-4-methylsulfanylmethoxy-cyclohexyl)-phenyl]-oxazolidin-2-one were obtained as a yellowish oil.

EXAMPLE 65

(RS)-3-[4-(trans-4-Methanesulfinylmethoxy-cyclohexyl)-phenyl]-5-methoxymethyl-oxazolidin-2-one (diastereomer mixture)

1.71 g (4.68 mmol) of (RS)-5-methoxymethyl-3-[4-(trans-4-methylsulfanylmethoxy-cyclohexyl)-phenyl]-oxazolidin-2-one were dissolved in 100 ml of methanol, cooled to 0° and treated dropwise while stirring during 40 minutes with a solution of 1.0 g (4.68 mmol) of sodium metaperiodate dissolved in 40 ml of water. The reaction mixture was held at about 4° for 24 hours. Thereafter, it was diluted with water and the product was extracted with methylene chloride. The organic phase was washed with water, dried over sodium sulfate and filtered. The filtrate was filtered through 50 g of silica gel 60 and washed separately with methanol. After evaporation of the methanol eluate the diastereomer mixture, (RS)-3-[4-(trans-4-methanesulfinylmethoxy-cyclohexyl)-phenyl]-5-methoxymethyl-oxazolidin-2-one, was crystallized from benzene. M.p.: 98°–100°.

EXAMPLE 66

(RS)-[trans-4-[4-(5-Methoxymethyl-2-oxo-oxazolidin-3-yl)-phenyl]-cyclohexyloxy]-acetonitrile 536.3 mg (1.40 mmol) of (RS)-3-[4-(trans-4-methanesulfinyl-methoxy-cyclohexyl)-phenyl]-5-methoxymethyl-oxazolidin-2-one (diastereomer mixture) were dissolved in 25 ml of abs. tetrahydrofuran and treated while stirring with 50 mg of zinc iodide and 465 mg (2.81 mmol) of trimethylsilyl cyanide. After stirring at room temperature for 21 hours the reaction mixture was diluted with 40 ml of methylene chloride and 40 ml of water and the organic phase was washed with water, dried over sodium sulfate, filtered and evaporated. The residue (517.5 mg) was chromatographed on 25 g of silica gel 60 with ethyl acetate/n-hexane (1:1). 90 mg of (RS)-[trans-4-(5-methoxymethyl-2-oxo-oxazolidin-3-yl)-phenyl]-cyclohexyloxy]-acetonitrile were obtained as a colorless oil. $^1$H-NMR (CDCl$_3$) ppm: 7.48 (d,2H), 7.20 (d,2H), 4.75 (m,1H), 4.32 (d,2H), 4.05 (t,1H), 3.92 (t,1H), 3.65 (d,2H), 3.60 (m,1H), 3.43 (s,3H), 2.50 (m,1H), 2.20 (d,2H), 1.95 (d,2H), 1.47 (bm,4H).

EXAMPLE 67

(RS)-3-[4-(trans-4-Methanesulfonylmethoxy-cyclohexyl)-phenyl]-5-methoxymethyl-oxazolidin-2-one 320.1 mg (0.88 mmol) of (RS)-5-methoxymethyl-3-[4-(trans-4-methylsulfanylmethoxy-cyclohexyl)-phenyl]-oxazolidin-2-one were dissolved in 15 ml of methylene chloride and treated with 226.9 mg (0.97 mmol) of m-chloroperbenzoic acid. After 3 hours at room temperature the reaction mixture was washed with sodium hydrogen carbonate solution and water and the organic phase was dried over sodium sulfate, filtered and evaporated. The residue (343.2 mg) was chromatographed on 20 g of silica gel 60 with ethyl acetate. After recrystallization from methylene chloride/ether 136.7 mg of (RS)-3-[4-(trans-4-methanesulfonylmethoxy-cyclohexyl)-phenyl]-5-methoxymethyl-oxazolidin-2-one were obtained as a white crystallizate of m.p. 145°–147°.

EXAMPLE 68

(RS)-3-[trans-4-[4-(5-Methoxymethyl-2-oxo-oxazolidin-3-yl)-phenyl]-cyclohexyloxy]ethanamine.HCl 189.7 mg (0.5508 mmol) of (RS)-[trans-4-[4-(5-methoxymethyl-2-oxo-oxazolidin-3-yl)-phenyl]-cyclohexyloxy]-acetonitrile were dissolved in 15 ml of methanol saturated with dry ammonia gas and hydrogenated in the presence of 300 mg of Raney-nickel (Type B 113W Degussa). After 30 minutes the catalyst was filtered off and the filtrate was evaporated. The residue was dissolved in methylene chloride, washed with water, dried over sodium sulfate, filtered and evaporated. The base was dissolved in alcohol and made acid with ethereal hydrochloric acid. After recrystallization from alcohol-ether there were obtained 186.0 mg of (RS)-3-[trans-4-[4-(5-methoxymethyl-2-oxo-oxazolidin-3-yl)-phenyl]-cyclohexyloxy]-ethanamine. HCl. M.p.: 204°–206°.

EXAMPLE 69

(RS)-3-[trans-4-[4-(5-Methoxymethyl-2-oxo-oxazolidin-3-yl)-phenyl]-cyclohexyloxy]-propylacetamide 199.5 mg (0.5 mmol) of (RS)-3-[trans-4-[4-(5-methoxymethyl-2-oxo-oxazolidin-3-yl)-phenyl]-cyclohexyloxy]-propanamine.HCl were dissolved in 5 ml of methylene chloride and treated with 43.2 mg (0.55 mmol) of acetyl chloride in the presence of 87.01 mg (1.1 mmol) of pyridine. After 3 hours the mixture was washed with water and the organic phase was dried over sodium sulfate, filtered and evaporated. After recrystallization from ethyl acetate/ether there were obtained 17.58 mg of (RS)-3-[trans-4-[4-(5-methoxymethyl-2-oxo-oxazolidin-3-yl)-phenyl]-cyclohexyloxy]-propylacetamide. M.p.: 72°–74°.

EXAMPLE 70

(R)-3-[trans-4-[4-(5-Methoxymethyl-2-oxo-oxazolidin-3-yl)-phenyl]-cyclohexyloxy]-propionitrile 4.58 g (15.0 mmol) of (R)-3-[trans-(4-hydroxycyclohexyl)-phenyl]-5-methoxymethyl-oxazolidin-2-one were dissolved in 400 ml of methylene chloride and treated in succession with 0.96 g (18.0 mmol) of acrylonitrile and 2.02 g (18.0 mmol) of potassium tert-butylate. The reaction mixture was stirred at room temperature for 16 hours. Thereafter, it was treated with water, insoluble material was filtered off over Dicalit and, the organic phase was washed with water, dried over sodium sulfate, filtered and evaporated. The residue (5.1 g) was chromatographed on 204 g of silica gel 60 with ethyl acetate/n-hexane (6:4). After recrystallization from tert-butyl methyl ether there were obtained 1.6 g of (R)-3-[trans-4-[4-(5-methoxymethyl-2-oxo-oxazolidin-3-yl)-phenyl]-cyclohexyloxy]-propionitrile. M.p.: 57°–59°. $[\alpha]_D$=–30.0° (c=0.7 in $CHCl_3$).

EXAMPLE 71

(R)-3-[trans-4-(3-Amino-propoxy)-cyclohexyl]-phenyl]-5-methoxymethyl-oxazolidin-2-one hydrochloride 932 mg (2.6 mmol) of (R)-3-[trans-4-[4-(5-methoxymethyl-2-oxo-oxazolidin-3-yl)-phenyl]-cyclohexyloxy]-propionitrile were dissolved in 60 ml of methanol saturated with dry ammonia gas and hydrogenated in the presence of 0.9 g of Raney-nickel (Type B 113W Degussa). After 3 hours the catalyst was filtered off under suction and the filtrate was evaporated. The residue was dissolved in methylene chloride, washed with water, dried over sodium sulfate, filtered and evaporated. The base was dissolved in alcohol and made acid with ethereal hydrochloric acid. After recrystallization from alcohol-ether there were obtained 825.2 mg of (R)-3-[trans-4-(3-amino-propoxy)-cyclohexyl]-phenyl]-5-methoxymethyl-oxazolidin-2-one.HCl. M.p.: 178°–180°. $[\alpha]_D$=–29.78° (c=1% in $CHCl_3$).

EXAMPLE 72

(R)-5-Methoxymethyl-3-[4-(4-methylenecyclohexyl)-phenyl]-oxazolidin-2-one 2.0 g (7.7 mmol) of [4-(4-methylenecyclohexyl)-phenyl]-ethoxycarbamic ester were stirred at 160° C. overnight with 1.02 g (7.7 mmol) of (S)-4-methoxymethyl-1,3-dioxolan-2-one and 170 mg of potassium carbonate. The residue was taken up in 50 ml of dichloromethane and extracted with 50 ml of water. The organic phase was dried with sodium sulfate and concentrated. After chromatography over silica gel with ethyl acetate/hexane 1:99 and recrystallization from hexane there were obtained 1.04 g (45%) of (R)-5-methoxymethyl-3-[4-(4-methylenecyclohexyl)-phenyl]-oxazolidin-2-one, white crystals with m.p. 64°.

EXAMPLE 73

(R)-3-[4-(cis or trans-4-Hydroxy-4-methyl-cyclohexyl)-phenyl]-5-methoxymethyl-oxazolidin-2-one A solution of 945 mg (3 mmol) of mercuric acetate in 18 ml of water was treated with 18 ml of tetrahydrofuran. After stirring at room temperature for 30 minutes a solution of 900 mg (3 mmol) of (R)-5-methoxymethyl-3-[4-(4-methylenecyclohexyl)-phenyl]-oxazolidin-2-one in 18 ml of tetrahydrofuran was added dropwise to this suspension. After standing in a refrigerator for several days 18 ml of 2N sodium hydroxide solution were added and, after stirring for 30 minutes, a solution of 360 mg (9.5 mmol) of sodium borohydride in 12 ml of 2N sodium hydroxide solution was added. After stirring for 30 minutes the mixture was extracted with methylene chloride and the organic phase was washed with water and dried with sodium sulfate. After distillation of the solvent the residue was chromatographed over silica gel with ethyl acetate/dichloromethane (1:1). There were obtained 200 mg (21%) of (R)-3-[4-(cis-4-hydroxy-4-methyl-cyclohexyl)-phenyl]-5-methoxymethyl-oxazolidin-2-one as white crystals with m.p. 122°–123° and 500 mg of cis and trans mixture.

EXAMPLE 74

(R)-trans-5-Methoxymethyl-3-[4-(4-cyano-cyclohexyl)-phenyl]-oxazolidin-2-one

A suspension of 500 mg (1.84 mmol) of trans-[4-(4-cyano-cyclohexyl)-phenyl]-ethoxycarbamic acid, 365 mg (2.8 mmol) of (S)-4-methoxymethyl-1,3-dioxolan-2-one and 185 mg of potassium carbonate was stirred at 160° for 16 hours. The reaction mixture was chromatographed over silica gel with ethyl acetate/hexane 1:1 and the yellow crystals obtained were recrystallized from ethyl acetate. 165 mg (29%) were obtained as white crystals with m.p. 174°.

EXAMPLE 75

(RS)-5-Methoxymethyl-3-[4-(4-dimethylmethylene-cyclohexyl)-phenyl]-oxazolidin-2-one 1.60 g (3.3 mmol) of isopropyl-triphenylphosphonium bromide/sodium amide mixture in 30 ml of tetrahydrofuran were stirred at room temperature for 1 hour. Then, a solution of 1.0 g (3.3 mmol) of (RS)-3-[4-(4-oxo-cyclohexyl)-phenyl]-5-methoxymethyl-oxazolidin-2-one in 25 ml of tetrahydrofuran was added dropwise. After boiling at reflux over the weekend the mixture was poured into 100 ml of water and extracted three times with 50 ml of dichloromethane each time. After chromatography over silica gel with ethyl acetate/hexane 1:2 and recrystallization from n-hexane 120 mg (11%) were obtained as white crystals with m.p. 89°–91°.

EXAMPLE 76

Mixture of (RS)- and (SR)-3-[4-[(RS)-4-Benzyliden-cyclohexyl]-phenyl]-5-methoxymethyl-oxazolidin-2-one 5.0 g (10 mmol) of benzyl-triphenylphosphonium bromide/sodium amide mixture in 100 ml of tetrahydrofuran were stirred at room temperature for 1 hour. Then, a solution of 3.04 g (10 mmol) of (RS)-3-[4-(4-oxocyclohexyl)-phenyl]-5-methoxymethyl-oxazolidin-2-one in 150 ml of tetrahydrofuran in 150 ml of tetrahydrofuran was added dropwise and the mixture was boiled under reflux for 20 hours. After distillation of the solvent the residue was taken up with 150 ml of water and extracted four times with 80 ml of dichloromethane each time. After chromatography over silica gel with ethyl acetate/hexane 1:2 and recrystallization from ethyl acetate/hexane 250 mg (7%) were obtained as white crystals with m.p. 65°–69°.

EXAMPLE 77

(RS)-3-[4-(cis- and trans-4-Benzyl-cyclohexyl)-phenyl]-5-methoxymethyl-oxazolidin-2-one 290 mg of the mother liquor (of the foregoing procedure) in 40 ml of ethanol were treated with 100 mg of 10% palladium/charcoal and hydrogenated at room temperature for 20 hours. After chromatography over silica gel with ethyl acetate/hexane 1:2 there were obtained 110 mg of resin. MS: m/e (% basic peak): 379 ($M^+$, 100), 246 (23), 144 (31), 118 (26), (55), (26), 45 (28).

EXAMPLE 78

Mixture of (RS)- and (SR)-[4-[4-[(RS)-5-Methoxymethyl-2-oxo-3-yl]-phenyl]-cyclohexyliden]-acetic acid methylester 10.0 g (33 mmol) of (RS)-3-[4-(4-oxocyclohexyl)-phenyl]-5-methoxymethyl-oxazolidin-2-one and 11.0 g (33 mmol) of methoxycarbonylmethylene-triphenylphosphorane in 500 ml benzene were boiled under reflux for 24 hours. After distillation of the solvent in a vacuum the residue was chromatographed over silica gel with ethyl acetate/hexane 1:1. 3.6 g (43%) of white crystals with m.p. 62°–64° were obtained.

EXAMPLE 79

(RS)-3-(4-Cyclohexyl-3-nitro-phenyl)-5-methoxymethyl-oxazolidin-2-one 2.44 g (8.4 mmol) of (4-cyclohexyl-3-nitrophenyl)-ethoxycarbamic ester and 1.10 g (8.4 mmol) of (RS)-4-methoxymethyl-1,3-dioxolan-2-one and 200 mg of potassium carbonate were stirred at 160° for 1 day. After chromatography over silica gel with ethyl acetate/hexane 2:3 and recrystallization from ethyl acetate/ether there was obtained 0.94 g (34%) of beige crystals with m.p. 105°–106°.

EXAMPLE 80

(RS)-3-(3-Amino-4-cyclohexyl-phenyl)-5-methoxymethyl-oxazolidin-2-one 0.5 g (1.5 mmol) of (RS)-3-(4-cyclohexyl-3-nitrophenyl)-5-methoxymethyl-oxazolidin-2-one (from the mother liquor of the foregoing reaction) in 75 ml of ethanol was treated with 100 mg of 10 percent palladium-on-charcoal and hydrogenated at room temperature for 5 hours. Filtration, concentration and recrystallization from ethyl acetate gave 150 mg of white crystals with m.p. 130°–132°.

EXAMPLE 81

(RS)-3-(4-Cyclohexyl-3-iodo-phenyl)-5-methoxymethyl-oxazolidin-2-one 180 mg (0.6 mmol) of (RS)-3-(3-amino-4-cyclohexyl-phenyl)-5-methoxymethyl-oxazolidin-2-one (from the mother liquor of the foregoing reaction) were suspended in a mixture of 0.32 ml of water, 0.32 g of 37 percent hydrochloric acid and 0.64 g of ice and treated with a solution of 41.4 mg (0.6 mmol) of sodium nitrite in 0.3 ml of water at 0°–5°. After stirring at this temperature for 30 minutes a solution of 0.1 g (0.6 mmol) of potassium iodide in 0.3 ml of water was added. The mixture was stirred at room temperature overnight, extracted with ethyl acetate and chromatographed over silica gel with ethyl acetate/hexane 3:1 to give 100 mg of oil. MS: m/e (% basic peak): 415 ($M^+$, 100), 372 (5), 346 (9), 289 (9), 245 (12), 143 (15), 71 (22).

EXAMPLE 82

(RS)-3-(4-Cyclohexyl-3-hydroxy-phenyl)-5-methoxymethyl-oxazolidin-2-one 200 mg (0.7 mmol) of (RS)-3-(3-amino-4-cyclohexyl-phenyl)-5-methoxymethyl-oxazolidin-2-one were suspended in a mixture of 0.86 ml of water, 0.72 g of ice and 0.235 ml of conc. sulfuric acid and treated at 0°–50 with a solution of 45 mg (0.66 mmol) of sodium nitrite in 0.4 ml of water. After boiling under reflux for 3 hours the mixture was extracted with dichloromethane, dried with sodium sulfate and the solvent was distilled off. Chromatography over silica gel with ethyl acetate/hexane 1:2 gave 120 mg (60%) of white crystals with m.p. 207°–208°.

EXAMPLE 83

(RS)-3-(3-Chloro-4-cyclohexyl-phenyl)-5-methoxymethyl-oxazolidin-2-one 0.45 g (1.6 mmol) of 3-chloro-4-cyclohexylphenyl)-ethoxycarbamic ester and 0.84 g (6.4 mmol) of (RS)-4-methoxymethyl-1,3-dioxolan-2-one and 200 mg of potassium carbonate were stirred at 160° for 24 hours. Chromatography over silica gel with dichloromethane yielded 0.57 g of oil which still contained dioxolanone. This was removed by short-path distillation at 100°/0.2 mbar. 0.38 g (73%) of resin remained. MS: m/e (% basic peak) 323 ($M^+$, 100), 280 (13), 254 (13), 178 (25), 152 (18), 71 (36).

Preparation of the Intermediates

EXAMPLE 84

(RS)-3-(4-Cyclohexyl-phenylamino)-propane-1,2-diol 8.05 g (44.6 mmol) of 4-cyclohexylaniline, 12.0 g (57 mmol) of methanesulfonic acid (RS)-2,2-dimethyl-1,3-dioxolan-4-yl-methyl ester and 11.2 ml (80 mmol) of triethylamine were held at 140° in a bomb tube for 4 h. The solvent was distilled off in a water-jet vacuum and the brown oily residue was treated with 50 ml of 3N hydrochloric acid and stirred at 50° for 1 hour. After cooling the mixture was extracted twice with 250 ml of ether each time, the aqueous phase was made alkaline with 3N sodium hydroxide solution and the product was taken up in ethyl acetate. The organic phase was washed with water, dried over magnesium sulfate and the solvent was distilled off. The oily residue crystallized upon treatment with ethyl acetate/hexane. 2.2 g of crystalline (RS)-3-(4-cyclohexyl-phenylamino)-propane-1,2-diol were obtained. M.p.: 121°–122° (dec.). A further 0.65 g of crystalline product was obtained from the mother liquor.

EXAMPLE 85 a)
(S)-3-(4-Cyclohexyl-phenylamino-methyl)-4-(2,2-dimethyl-1,3-dioxolane)

5.0 g (28.5 mmol) of 4-cyclohexylaniline, 10.0 g (34.9 mmol) of (R)-2,2-dimethyl-1,3-dioxolan-4-methanol-toluene-4-sulfonate and 10 ml of triethylamine were stirred at an oil bath temperature of 140° for 3 hours. The brown oil obtained after distilling off the readily volatile constituents in a water-jet vacuum was treated with saturated sodium carbonate solution and extracted with ethyl acetate. The organic phase was washed with sodium chloride solution, dried over magnesium sulfate and the solvent was distilled off. There were obtained 9.5 g of a brown oil which was chromatographed on a 30-fold amount of silica gel. After elution with ethyl acetate-hexane (1:3) the fractions which were uniform according to tlc (ethyl acetate-hexane 1:2) were pooled and the solvent was distilled off. 9.4 g of a yellowish oil were obtained. B.p.: 140°/0.01 mbar. $[\alpha]_D$=+1.43 (c=1, CHCl$_3$).

b)
(S)-3-(4-Cyclohexyl-phenylamino)-propane-1,2-diol 4.5 g of (S)-3-(4-cyclohexyl-phenylamino-methyl)-4-(2,2-dimethyl-1,3-dioxolane) were treated with 50 ml of 3N hydrochloric acid and stirred at 50° for 1 hour. After cooling the mixture was made alkaline with 3N sodium hydroxide solution while cooling with ice and the separated oil was taken up in ethyl acetate, washed with sodium chloride solution, dried over magnesium sulfate and the solvent was distilled off. The pale brown oil obtained (4.1 g) was chromatographed on a 30-fold amount of silica gel. The methylene fractions were discarded and the ethyl acetate-methylene chloride (1:1) fractions were pooled. 1.5 g of product were obtained in the form of beige crystals. M.p.: 116°. $[\alpha]_D$=–12.5° (c=0.6, CHCl$_3$).

EXAMPLE 86 a)
(R)-3-(4-Cyclohexyl-phenylamino-methyl)-4-(2,2-dimethyl-1,3-dioxolane)

10.0 g (57 mmol) of 4-cyclohexylaniline were reacted with 20.0 g (70 mmol) of (S)-2,2-dimethyl-1,3-dioxolane-4-methanol-toluene-4-sulfonate as given in Example 42 a) and worked up. 11.7 g (71%) of a yellowish oil were obtained. $[\alpha]_D$=–2.4 (c=1.0, CHCl$_3$).

b)
(R)-3-(4-Cyclohexyl-phenylamino)-propane-1,2-diol 11.5 g of (R)-3-(4-cyclohexyl-phenylamino-methyl)-4-(2, 2-dimethyl-1,3-dioxolane) were reacted with 100 ml of 3N hydrochloric acid as given in Example 42 b) and worked up. 6.25 g of product were obtained in the form of beige crystals. M.p.: 118°–120°. $[\alpha]_D$=–12.75 (c=0.4, CHCl$_3$).

EXAMPLE 87

[4-(4-Oxo-cyclohexyl)-phenyl]-ethoxycarbamic ester 10.0 g (52.8 mmol) of 4-(4-aminophenyl)-cyclohexanone were dissolved in 150 ml of tetrahydrofuran. After adding 10 ml of water and 6.65 g (79.2 mmol) of sodium bicarbonate the mixture was stirred intensively for 15 minutes and subsequently a solution of 5.5 ml of ethyl chloroformate (58.1 mmol) ein 25 ml of tetrahydrofuran was added dropwise within 20 minutes, during which the temperature should not exceed 20°. After 2 hours the separated precipitate was filtered off under suction and the solvent was distilled off in a water-jet vacuum. The oily residue was treated with water and the reaction product was extracted with ethyl acetate. The organic phase was washed with water, dried over magnesium sulfate and the solvent was distilled off. 13.89 g (100%) of carbamate were obtained. M.p.: 160°–162°.

EXAMPLE 88 a) 1-(4-Aminophenyl)-4-piperidinone 5.6 g of 1-(4-nitrophenyl)-4-piperidone were suspended in 60 ml of dioxan under argon, treated with 2.6 ml of triethylamine and 0.6 g of palladium-on-charcoal (5%) and hydrogenated at room temperature and normal pressure. Filtration and concentration yielded 5.0 g of 1-(4-aminophenyl)-4-piperidinone.

b) Ethyl 4-(4-oxo-piperidin-1-yl)-phenylcarbamate 4.9 g of 1-(4-aminophenyl)-4-piperidinone were suspended in a mixture of 30 ml of tetrahydrofuran and 9 ml of water under argon and treated with 3.3 g of sodium hydrogen carbonate. Then, a solution of 2.7 ml of ethyl chloroformate in 20 ml of tetrahydrofuran was added dropwise at room temperature while stirring vigorously and, after completion of-the addition, the mixture was stirred for a further 1 h. After adding water and ethyl acetate the phases were separated and the aqueous phase was extracted with ethyl acetate. The organic phases were combined, dried with magnesium sulfate and concentrated. The residue (6.6 g) was chromatographed over silica gel 60 with ethyl acetate/hexane mixtures (1:2–1:0). Crystallization from diethyl ether yielded 3.8 g of ethyl 4-(4-oxo-piperidin-1-yl)-phenylcarbamate as grey crystals. M.p.: 145°–146°.

EXAMPLE 89 a) (RS)-3-(5-Bromo-pyridin-2-yl)-5-methoxy-methyl-oxazolidin-2-one

A mixture of 9.3 g of ethyl 5-bromo-pyridin-2-yl-carbamate, 7.5 g of 4-methoxymethyl-1,3-dioxolan-2-one, 1.0 g of potassium carbonate and 10 ml of decahydronaphthalene was heated to 160° C. for 6 h. The mixture was cooled and treated with ethyl acetate and water. The phases were separated, the aqueous phase was extracted with ethyl acetate and the organic phase was washed with saturated sodium chloride solution. The organic phases were combined and dried with magnesium sulfate and then concentrated. Chromatography of the residue (20.2 g) with ethyl acetate/hexane mixtures (1:2–1:1) on silica gel yielded 6.4 g of (RS)-3-(5-bromo-pyridin-2-yl)-5-methoxy-methyl-oxazolidin-2-one which was recrystallized from diethyl ether. M.p.: 90°–92°.

b) (RS)-3-[5-(1,4-Dioxa-Spiro[4,5]dec-7-en-8-yl)-pyridin-2-yl]-5-methoxymethyl-oxazolidin-2-one A suspension of 1.4 g of 3-(5-bromo-pyridin-2-yl)-5-methoxymethyl-oxazolidin-2-one, 1.4 g of 8-trimethylstannyl-1,4-dioxa-spiro[4,5]dec-7-ene and 0.3 of bis(triphenylphosphine)palladium(II) dichloride in 20 ml of tetrahydrofuran was stirred at 70° under argon for 18 h. Then, the mixture was cooled, treated with 150 ml of ethyl acetate and 150 ml of saturated potassium fluoride solution and stirred for 30 minutes. The mixture was filtered over a Celite® pad, the phases were separated and the aqueous phase was extracted with ethyl acetate. The organic phases were combined, dried with magnesium sulfate, concentrated and chromatographed over silica gel 60 with diethyl ether as the eluent. There was obtained 0.6 g of (RS)-3-[5-(1,4-dioxa-spiro[4,5]dec-7-en-8-yl)-pyridin-2-yl]-5-methoxymethyl-oxazolidin-2-one. $^1$H-nmr(CDCl$_3$) ppm: 8.41 (s, 1H), 8.03 (d, 1H), 7.89 (d, 1H), 6.08 (t, 1H), 4.82 (m, 1H), 4.21 (t, 1H), 3.91 (t, 1H), 3.92 (s, 4H), 3.60 (m, 2H), 3.32 (s, 3H), 2.54 (m, 2H), 2.38 (m, 2H), 1.82 (t, 2H).

EXAMPLE 90 a) Trifluoromethanesulfonic acid 1,4-dioxa-spiro[4,5]dec-7-en-8-yl ester

A lithium diisopropylamide solution was prepared in 1 l of absolute tetrahydrofuran under argon from 48 ml of diisopropylamine and 210 ml of a 1.6M solution of n-butyllithium in hexane. A solution of 50 g of 1,4-cyclohexanedione monoethylene ketal in 200 ml of tetrahydrofuran was added dropwise to this solution at –70°. After removing the cooling the mixture reached –20°, was then again cooled to -70° and treated rapidly with 120 g of N-phenyl-bis(trifluoromethanesulfonimide) in 500 ml of tetrahydrofuran. After removing the cooling the mixture reached room temperature and was concentrated. The residue (215 g) was filtered over silica gel 60 with ethyl acetate/hexane (1:9). Trifluoromethanesulfonic acid 1-4-dioxa-spiro[4,5]dec-7-en-8-yl ester was obtained in quantitative yield. $^1$H-NMR (CDCl$_3$) ppm: 5.66 (m, 1H), 3.99 (s, 4H), 2.53 (m, 2H), 2.42 (m, 2H), 1.90 (t, 2H).

b) 8-Tributyl-stannyl-1,4-dioxa-spiro[4,5]dec-7-ene

A lithium diisopropylamide solution was prepared in 400 ml of absolute tetrahydrofuran under argon from 13 ml of diisopropylamine and 59 ml of a 1.6M solution of n-butyllithium in hexane. 21 ml of tributyltin hydride were added dropwise to this solution at –70° and the mixture was stirred for 2 h. After adding 3.5 g of copper(I) cyanide the mixture was left to warm to –50° and a solution of 10.4 g of trifluoromethanesulfonic acid 1,4-dioxa-spiro[4,5]dec-7-en-8-yl ester in 80 ml of tetrahydrofuran was rapidly added dropwise. The reaction solution slowly became red in color while stirring at –30° for 2 h. The cooling was removed and the mixture was treated with saturated amonium chloride solution and hexane. After filtration over a Celite®°pad the aqueous phase was separated and the organic phase was washed in succession with water and saturated sodium chloride solution. The organic phase was dried with magnesium sulfate and concentrated. The residue was taken up in 300 ml of ethyl acetate, treated with 18 g of silver acetate and stirred in the air. The mixture was filtered over a Celite® pad and the filtrate was washed with water and saturated sodium chloride solution. The organic phase was dried with magnesium sulfate, concentrated and chromatographed over silica gel 60 (deactivated with triethylamine). There were obtained 8.9 g of 8-tributyl-stannyl-1,4-dioxa-spiro[4,5]dec-7-ene. $^1$H-nmr (CDCl$_3$) ppm: 5.70 (m, 1H), 3.98 (s, 4H), 2.36 (bm, 4H), 1.74 (t, 2H), 1.45 (m, 6H), 1.30 (m, 6H), 0.88 (m, 9H).

EXAMPLE 91 a) (RS)-5-Methoxymethyl-3-pyridin-3-yl-oxazolidin-2-one

A mixture of 16.8 g of ethyl pyridin-3-yl-carbamate, 20 g of 4-methoxymethyl-1,3-dioxolan-2-one and 2.8 g of potassium carbonate was heated to 160° for 3 h. The mixture was cooled and treated with ethyl acetate and water. The phases were separated, the aqueous phase was extracted with ethyl acetate and the organic phase was washed with saturated sodium chloride solution. The organic phases were combined, dried with magnesium sulfate and concentrated. Chromatography of the residue (21 g) on silica gel with ethyl acetate/methanol mixtures (1:0–20:1) yielded 17.6 g of (RS)-5-methoxymethyl-3-pyridin-3-yl-oxazolidin-2-one which was recrystallized from diethyl ether. M.p.: 65°–66°.

b) (RS)-5-Methoxymethyl-3-(1-oxy-pyridin-3-yl)-oxazolidin-2-one 33.4 g of 3-chloroperbenzoic acid were added under argon to a solution of 16.5 g of (RS)-5-methoxymethyl-3-pyridin-3-yl-oxazolidin-2-one in 250 ml of methylene chloride and the mixture was stirred at room temperature for 4 h. Subsequently, the mixture was washed with water and the aqueous phase was extracted with methylene chloride. The organic phases were combined, dried with magnesium sulfate, concentrated and chromatographed over silica gel with methylene chloride/methanol mixtures (50:1–20:1). The product, 15.9 g of (RS)-5-methoxymethyl-3-(1-oxy-pyridin-3-yl)-oxazolidin-2-one, was boiled with diethyl ether for further purification. M.p.: 82°–83°.

c) (RS)-3-(6-Bromo-1-oxy-pyridin-3-yl)-5-methoxymethyl-oxazolidin-2-one 5.9 ml of bromine dissolved in 35 ml of methylene chloride were added dropwise at room temperature to a solution of 25.5 g of (RS)-5-methoxymethyl-3-(1-oxy-pyridin-3-yl)-oxazolidin-2-one in 300 ml of methylene chloride under argon. The mixture was stirred for a further 3 h., then treated with 350 ml of sodium hydrogen carbonate and finally the phases were separated. The aqueous phase was extracted several times more with methylene chloride. The organic phases were combined, dried with magnesium sulfate, concentrated and chromatographed over silica gel 60 with methylene chloride/methanol mixtures (50:1–20:1). Chromatography yielded 22.5 g of (RS)-3-(6-bromo-1-oxy-pyridin-3-yl)-5-methoxymethyl-oxazolidin-2-one. $^1$H-nmr (CDCl$_3$) ppm: 8.54 (s, 1H), 7.74 (d,1H), 7.59 (d, 1H), 4.82 (m, 1H), 4.00 (t, 1H), 3.90 (t, 1H), 3.66 (m, 2H), 3.43 (s, 3H).

d)
(RS)-3-(6-Bromo-pyridin-3-yl)-5-methoxymethyl-oxazolidin-2-one 10.5 ml of phosphorus tribromide were added dropwise to a boiling solution of 22.5 g of (RS)-3-(6-bromo-1-oxy-pyridin-3-yl)-5-methoxymethyl-oxazolidin-2-one in methylene chloride under argon and the mixture was boiled overnight. Subsequently, the mixture was cooled and poured into 300 ml of 2N sodium hydroxide solution while stirring vigorously. The aqueous phase was extracted several times with methylene chloride and the organic phases were combined, dried with magnesium sulfate and concentrated. The residue (11.3 g) was chromatographed over silica gel 60 with methylene chloride as the eluent. Chromatography yielded 9.9 g of (RS)-3-(6-bromo-pyridin-3-yl)-5-methoxymethyl-oxazolidin-2-one which was boiled with diethyl ether for further purification. M.p.: 108°–110°.

EXAMPLE 92

(RS)-3-[6-(1,4-Dioxa-spiro[4,5]dec-7-en-8-yl)pyridin-3-yl]-5-methoxymethyl-oxazolidin-2-one A suspension of 8.9 g of (RS)-3-(6-bromo-pyridin-3-yl)-5-methoxymethyl-oxazolidin-2-one, 6.5 g of 8-tributyl-stannyl-1,4-dioxaspiro[4,5]dec-7-ene and 1.4 g of bis(triphenylphosphine)palladium(II) dichloride in 40 ml of dimethylformamide was stirred at 85° under argon for 22 h. Then, the mixture was cooled, filtered over a Celite® pad, the filter cake was washed with a large amount of ethyl acetate and the organic phase was washed several times with semi-saturated sodium chloride solution. The aqueous phases were extracted with ethyl acetate, the organic phases were combined, concentrated to a volume of 250 ml, treated with 250 ml of saturated potassium fluoride solution and stirred for 30 minutes. The mixture was again filtered over a Celite® pad, the phases were separated and the aqueous phase was extracted with ethyl acetate. The organic phases were combined, dried with magnesium sulfate, concentrated and chromatographed over silica gel 60 with diethyl ether as the eluent. There were obtained 1.2 g of (RS)-3-[6-(1,4-dioxa-spiro[4,5]dec-7-en-8-yl)-pyridin-3-yl]-5-methoxymethyl-oxazolidin-2-one. $^1$H-nmr (CDCl$_3$) ppm: 8.48 (s, 1H), 8.19 (d, 1H), 7.56 (d,1H), 6.50 (m, 1H), 4.79 (m, 1H), 4.12 (t, 1H), 4.02 (s, 4H), 3.98 (t, 1H), 3.64 (m, 2H), 3.44 (s, 3H), 2.80 (m, 2H), 2.52 (m, 2H), 1.96 (t, 2H).

EXAMPLE 93

Ethyl 4-cycloheptylphenyl-carbamate 6.81 g (36.0 mmol) of 4-aminophenyl-cycloheptane were dissolved in 60 ml of methylene chloride and treated with 3.13 g (39.6 mmol) of pyridine. The reaction mixture was treated dropwise at room temperature while stirring with a solution of 4.3 g (39.6 mmol) of ethyl chloroformate in 15 ml of methylene chloride. After 2 hours the mixture was washed with water and the organic phase was dried over sodium sulfate, filtered and evaporated. The ethyl 4-cycloheptylphenyl-carbamate distilled at 165°–170° and 0.3 mbar.

EXAMPLE 94

Ethyl 4-(adamantan-1-yl)-phenyl-carbamate 5.28 g (20 mmol) of 4-adamantan-1-yl-phenylamine hydrochloride were placed in 100 ml of methylene chloride and treated with 3.22 g (42.0 mmol) of pyridine. A solution of 2.39 g (22.0 mmol) of ethyl chloroformate in 15 ml of methylene chloride was added dropwise to this suspension at room temperature while stirring during 15 minutes. The reaction mixture was stirred at room temperature for 2 hours. Subsequently, the mixture was washed with water and the organic phase was dried over sodium sulfate, filtered and evaporated. The residue was recrystallized from methylene chloride/n-hexane. 5.6 g of ethyl 4-adamantan-1-yl-phenyl-carbamate were obtained as a white crystallizate. M.p.: 132°–134°.

EXAMPLE 95

Mixture of (R)- and (S)-[4-[4-[(R)-5-Methoxymethyl-2-oxo-oxazolidin-3-yl]-phenyl]-cyclohexylidene-acetonitrile 0.66 g of sodium were dissolved in 70 ml of ethanol under argon. Thereafter, 5.08 g (=4.51 ml) of diethyl cyanomethylphosphonate dissolved in 20 ml of ethanol were added at 20°. The mixture was stirred at room temperature for 30 minutes and then 2.9 g of (R)-5-methoxymethyl-3-[4-(4-oxo-cyclohexyl)-phenyl]-oxazolidin-2-one were added. Thereafter, the reaction mixture was stirred at reflux for a further 1 hour, cooled to room temperature, adjusted to pH 6 with about 1 ml of glacial acetic acid and evaporated in a vacuum. The residue was dissolved in dichloromethane and washed three times with water, subsequently dried and evaporated. The excess phosphoric ester, which was still present in the residue, was distilled off at a bath temperature of ~100° and 0.03 mm vacuum (bP$_{0.03}$ 34°). The residue remaining (3.2 g) was chromatographed over 250 g of silica gel using medium pressure. Elution was carried out with dichloromethane, dichloromethane/ethyl acetate 20:1. The fractions which were pure according to thin-layer chromatography were combined and concentrated in a vacuum. 2.6 g of mixture of (R)- and (S)-[4-[4-[(R)-5-methoxymethyl-2-oxo-oxazolidin-3-yl]-phenyl]-cyclohexylidene]-acetonitrile (~1:2 E/Z or Z/E) were obtained as a slightly turbid oil. This was used directly for the reduction.

EXAMPLE 96 t-Butyl 4-(4-nitrophenyl)-piperidine-1-carboxylate 7.63 g (37.0 mmol) of 4-(4-nitrophenyl)piperidine and 8.88 g (40.7 mmol) of di-tert-butyl dicarbonate were stirred at room temperature in 150 ml of chloroform for 4 hours. Thereafter, the mixture was washed with water and the organic phase was dried over sodium sulfate, filtered and evaporated. After recrystallization from n-hexane there were obtained 11.2 g of t-butyl 4-(4-nitrophenyl)-piperidine-1-carboxylate. M.p.: 60°–62°.

EXAMPLE 97 t-Butyl 4-(4-aminophenyl)-piperidine-1-carboxylate 11.03 g (36.0 mmol) of t-butyl 4-(4-nitrophenyl)-piperidine-1-carboxylate were dissolved in 200 ml of alcohol and hydrogenated at room temperature and normal pressure in the presence of 1 g of palladium-on-charcoal (10%). After filtration of the catalyst the filtrate was concentrated and the residue (10.0 g) in methylene chloride was washed with water. After recrystallization from ether/n-hexane there were obtained 8.0 g of t-butyl 4-(4-aminophenyl)-piperidine-2-carboxylate. M.p.: 114°–116°.

EXAMPLE 98 t-Butyl 4-(4-ethoxycarbonylamino-phenyl)-piperidine-1-carboxylate 8.84 g (32.0 mmol) of t-butyl 4-(4-aminophenyl)-piperidine-1-carboxylate were dissolved in 150ml of methylene chloride and treated with 3.82 g (35.2 mmol) of ethyl chloroformate in the presence of 2.78 g (35.2 mmol) of pyridine. The reaction mixture was stirred at room temperature for 16 hours. Thereafter, it was washed with water and the organic phase was dried over sodium sulfate, filtered and evaporated. The residue (11.3 g) was chromatographed on 95 g of silica gel 60 with ether/n-hexane (4:6). After recrystallization from ether/n-hexane there were obtained 6.15 g of t-butyl 4-(4-ethoxycarbonylamino-phenyl)-piperidine-1-carboxylate. M.p.: 126°–128°.

EXAMPLE 99

Ethyl 4-(4-ethoxycarbonylamino-phenyl)-piperidine-1-carboxylate 3.01 g (14.6 mmol) of 4-(4-aminophenyl)piperidine were dissolved in 100 ml of methylene chloride and treated while stirring with 1.74 g (16.06 mmol) of ethyl chloroformate in the presence of 11.55 g (146 mmol) of pyridine. After 3 hours the mixture was evaporated, the residue was partitioned in ethyl acetate/water and the organic phase was washed with water, dried over sodium sulfate, filtered and evaporated. The residue (2.7 g) was chromatographed on 85 g of silica gel 60 with methylene chloride/methanol (98:2). After recrystallization from ether/n-hexane there was obtained 0.9 g of ethyl 4-(4-ethoxycarbonylamino-phenyl)-piperidine-1-carboxylate. M.p.: 105°–107°.

EXAMPLE 100

4-[4-(Methylene-cyclohexyl)-phenyl]-ethoxycarbamic ester

A suspension of 15.95 g of methyltriphenylphosphonium bromide/sodium amide mixture (38.3 mmol of methyltriphenylphosphonium bromide) in 300 ml was stirred at room temperature for 1 hour. Then, a solution of 10.0 g (38.3 mmol) of [4-(4-oxo-cyclohexyl)-phenyl]-ethoxycarbamic ester in 120 ml of tetrahydrofuran was added and the mixture was boiled under reflux overnight. The solvent was distilled off and the residue was chromatographed over silica gel with ethyl acetate/hexane 1:3. This gave 6.1 g (61%) of [4-(4-methylene-cyclohexyl)-phenyl]-ethoxycarbamic ester as white crystals with m.p. 98°.

EXAMPLE 101 cis- and trans-4-(4-Cyano-cyclohexyl)-aniline 392 mg (3.5 mmol) of potassium t-butylate were added portionwise at −10° to a suspension of 278 mg (1.5 mmol) of 4-(4-oxo-cyclohexyl)-aniline and 370 mg (1.9 mmol) of toluene-4-sulfonylmethylisocyanide in 5 ml of 1,2-dimethoxyethane and 0.15 ml of ethanol. After stirring at −5° for 1 hour and at room temperature for a further 70 hours 25 ml of water and 10 ml of saturated sodium chloride solution were added and the mixture was extracted three times with 40 ml of dichloromethane each time. The organic phase was dried with sodium sulfate and concentrated. Chormatography over silica gel with ethyl acetate/hexane 1:2 gave 165 mg (56%) of 4-(4-cyano-cyclohexyl)-aniline with m.p. 132°–140°.

EXAMPLE 102 cis-[4-(4-Cyano-cyclohexyl)-phenyl]ethoxycarbamic ester and trans-[4-(4-cyano-cyclohexyl)-phenyl]ethoxycarbamic ester To a solution of 2.75 g (14 mmol) of cis- and trans-4-(4-cyano-cyclohexyl)-aniline in 50 ml of tetrahydrofuran and 4 ml of water were added 1.74 g (21 mmol) of sodium hydrogen carbonate and, after 15 minutes, 1.46 ml (15.3 mmol) of ethyl chloroformate dissolved in 5 ml of tetrahydrofuran. After stirring at room temperature for 4 days the solvent was distilled off and the residue was suspended in 100 ml of dichloromethane and extracted with water and saturated sodium chloride solution. The organic phase was dried with sodium sulfate and concentrated. Chromatography of the residue over silica gel with ethyl acetate/hexane 1:2 yielded 630 mg (17%) of trans-[4-(4-cyano-cyclohexyl)-phenyl]ethoxycarbamic ester as white crystals with m.p. 145° and 80 mg (2%) of cis-[4-(4-cyano-cyclohexyl)-phenyl]ethoxycarbamic ester as white crystals with m.p. 110°, as well as 2.5 g (67%) of a cis-trans mixed fraction.

EXAMPLE 103

4-Cyclohexyl-3-nitrophenyl-ethoxycarbamic ester

A mixture of 1.97 g (8.9 mmol) of 4-cyclohexyl-3-nitroaniline and 1.13 g (13.4 mmol) of sodium hydrogen carbonate in 25 ml of tetrahydrofuran and 1.7 ml of water was treated with 1.07 g (9.9 mmol) of ethyl chloroformate dissolved in 5 ml of tetrahydrofuran. After stirring at room temperature overnight the solvent was distilled off and the residue was chromatographed over silica gel with ethyl acetate/hexane. 2.44 g (93%) of yellow oil were obtained. MS: m/e (% basic peak): 292 ($M^+$, 7), 275 (100), 247 (14), 229 (27), 201 (18), 41 (26).

EXAMPLE 104

3-Chloro-4-cyclohexylaniline

A mixture of 1.0 g (5 mmol) of 4-cyclohexyl-nitrobenzene and 0.1 g of iron(III) chloride was heated to 60°. After the cyclohexyl-nitrobenzene had melted chlorine gas was conducted through the well-stirred mixture for 15 minutes. Then, 20 ml of ice-water were added and the mixture was extracted with ether. The ether was distilled off and the residue was dissolved in 60 ml of methanol. Then, the solution was treated with 2.5 g (25 mmol) of copper(I) chloride and portionwise with 1.6 g (29 mmol) of potassium borohydride. After stirring for 30 minutes the mixture was poured into 0.5 l of water and extracted with ether. Drying over sodium sulfate, distillation of the ether and chromatography over silica gel with hexane/ethyl acetate 9:1 gave 0.68 g of oil. MS: m/e (% basic peak)=209 (M$^+$, 75), 166 (100), 140 (78), 131 (62).

EXAMPLE 105

(3-Chloro-4-cyclohexylphenyl)-ethoxycarbamic ester

A mixture of 0.59 g (2.8 mmol) of 3-chloro-4-cyclohexylaniline and 0.36 g (4.2 mmol) of sodium hydrogen carbonate in 10 ml of tetrahydrofuran and 0.75 ml of water was treated with 0.34 g (3.1 mmol) of ethyl chloroformate dissolved in 1 ml of tetrahydrofuran. After stirring at room temperature for 5 hours the mixture was poured into 25 ml of water and extracted with dichloromethane. Chromatography over silica gel with hexane/dichloromethane 2:1 gave 0.47 g (59%) of oil. MS: m/e (% basic peak)=281 (M$^+$, 100), 238 (18), 225 (12), 212 (34), 192 (23), 166 (19), 140 (20).

EXAMPLE A (RS)-3-(4-Cyclohexyl-phenyl)-5-hydroxymethyl-oxazolidin-2-one can be formulated as the active ingredient according to known methods to give pharmaceutical preparations of the following composition:

1. 100 mg capsules

| | |
|---|---|
| Active ingredient | 100.0 mg |
| Powd. lactose | 104.7 mg |
| Talc | 12.0 mg |
| Magnesium stearate | 3.0 mg |
| Corn starch | 70.0 mg |
| Hydroxypropylmethylcellulose | 10.0 mg |
| Dioctyl sodium sulfosuccinate | 0.3 mg |
| | 300 mg |

2. 50 mg tablets

| | |
|---|---|
| Active ingredient | 50.0 mg |
| Powd. lactose | 50.0 mg |
| Microcrystalline cellulose | 82.0 mg |
| Na carboxymethylstarch | 15.0 mg |
| Magnesium stearate | 3.0 mg |
| | 200 mg |

3. 500 mg suppositories

| | |
|---|---|
| Active ingredient | 500 mg |
| Suppository mass | ad 2000 mg |

4. 500 mg suppositories

| | |
|---|---|
| Active ingredient | 500 mg |
| Suppository mass | ad 2000 mg |

5. 100 mg soft gelatine capsules

| | |
|---|---|
| Active ingredient | 100 mg |
| Medium chain triglyceride | 300 mg |
| | 400 mg |

We claim:
1. A compound of the formula wherein

R is hydrogen or lower alkyl;

$Y^1$ is —CH=;

$Y^2$ is —CH=, —C(OH)=, —C(NO$_2$)=, —C(NH$_2$), or —C(Hal)=;

X is $C_3$–$C_7$ cycloalkenyl; unsubstituted bicyclo[2.2.1]hept-2-yl; bicyclo[2.2.1]hept-2-yl substituted by phenyl-2-oxo-5-methoxymethyloxazolidinyl; bicyclo[2.2.1]-hept-5-en-2-yl; adamantyl; unsubstituted $C_3$–$C_7$ cycloalkyl; or $C_3$–$C_7$ cycloalkyl substituted by halogen, amino, lower alkyl, nitrilo, oxo, hydroxyimino, ethylenedioxy, —OR$^1$, =CR$^2$R$^3$, —(CH$_2$)$_n$R$^4$, —COR$^5$, or —NR$^6$R$^7$, wherein R$^1$ is CH(C$_6$H$_5$)$_2$, —(CH$_2$)$_n$C$_6$H$_5$, lower alkyl, hydrogen, —(CH$_2$)$_n$NHCOCH$_3$, —(CH$_2$)$_n$NH$_2$, —(CH$_2$)$_n$CN, —(CH$_2$)SCH$_3$, —(CH$_2$)$_n$SO$_2$CH$_3$, —CO-lower alkyl, or —COC$_6$H$_5$;

R$^2$ is hydrogen or lower alkyl;

R$^3$ hydrogen, nitrilo, lower alkyl, phenyl or COO-lower-alkyl;

R$^4$ is nitrilo, amino, —NHCOCH$_3$, —COC$_6$H$_5$Hal, phenyl or hydroxy;

R$^5$ is lower alkyl, —CH=CH—C$_6$H$_5$, —C$_6$H$_5$CF$_3$, —O—C(CH$_3$)$_3$ or —O-lower-alkyl;

R$^6$ is hydrogen or —COCH$_3$;

R$^7$ is —COCH$_3$, benzyl or —(CH$_2$)$_n$NHCOC$_6$H$_4$Hal; and n is 1–3;

or a pharmaceutically acceptable acid addition salt thereof.

2. A compound according to claim 1, wherein $Y^2$ is —CH=.

3. A compound according to claim 2, wherein

X is unsubstituted bicyclo[2.2.1]hept-2-yl; bicyclo[2.2.1]hept-2-yl substituted by phenyl-2-oxo-5-methoxymethyloxazolidinyl; bicyclo[2.2.1]-hept-5-en-2-yl; adamantyl; unsubstituted $C_3$–$C_7$ cycloalkyl; or $C_3$–$C_7$ cycloalkyl substituted by halogen, lower alkyl, oxo, hydroxyimino, ethylenedioxy, —OR$^1$, =CR$^2$R$^3$, —(CH$_2$)$_n$R$^4$, or —NR$^6$R$^7$, wherein R$^1$ is lower alkyl, hydrogen, —(CH$_2$)$_n$NH$_2$ wherein n is 3, or —(CH$_2$)$_n$CN wherein n is 2, —CO-lower alkyl, or —COC$_6$H$_5$;

R$^2$ is hydrogen;

R$^3$ is hydrogen;

R$^4$ is hydroxy;

R$^6$ is H; and

R$^7$ is —(CH$_2$)$_n$NHCOC$_6$H$_4$Hal wherein n is 1–3.

4. A compound according to claim 3, wherein R is hydrogen or methyl.

5. A compound according to claim 4, wherein X is cyclohexyl; cyclohexyl substituted by oxo, hydroxyimino, or —OR$^1$ and wherein R$^1$ is lower alkyl, hydrogen, —(CH$_2$)$_n$NH$_2$ wherein n is 3, or —(CH$_2$)$_n$CN wherein n is 2.

6. A compound according to claim 3, wherein X is unsubstituted bicyclo[2.2.1]hept-2-yl or bicyclo[2.2.1]-hept-5-en-2-yl.

7. A compound according to claim 2, wherein R is methyl.

8. A compound according to claim 7, wherein X is cyclohexyl substituted by —OR$^1$, —(CH$_2$)$_n$R$^4$, or —COR$^5$,
wherein
R$^1$ is —(CH$_2$)$_n$NH$_2$ wherein n is 1, or —(CH$_2$)$_n$CN wherein n is 1;
R$^4$ is nitrilo and n is 1; and
R$^5$ is —CH=CH—C$_6$H$_5$.

9. A compound according to claim 8, (R)-[trans-4-[4-(5-methoxymethyl-2-oxo-oxazolidin-3-yl)-phenyl]-cyclohexyloxy]-acetonitrile.

10. A pharmaceutical composition comprising a therapeutically effective amount of a compound of the formula

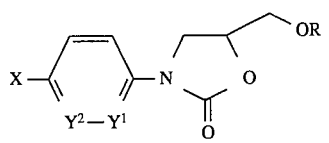

I wherein
R is hydrogen or lower alkyl;
Y$^1$ is —CH=;
Y$^2$ is —CH=, —C(OH)=, —C(NO$_2$)=, —C(NH$_2$), or —C(Hal)=;
X is C$_3$–C$_7$ cycloalkenyl; unsubstituted bicyclo[2.2.1]hept-2-yl; bicyclo[2.2.1]hept-2-yl substituted by phenyl-2-oxo-5-methoxymethyloxazolidinyl; bicyclo[2.2.1]-hept-5-en-2-yl; adamantyl; unsubstituted C$_3$–C$_7$ cycloalkyl; or C$_3$–C$_7$ cycloalkyl substituted by halogen, amino, lower alkyl, nitrilo, oxo, hydroxyimino, ethylenedioxy, —OR$^1$, =CR$^2$R$^3$, —(CH$_2$)$_n$R$^4$, —COR$^5$, or —NR$^6$R$^7$
wherein
R$^1$ is CH(C$_6$H$_5$)$_2$, —(CH$_2$)$_n$C$_6$H$_5$, lower alkyl, hydrogen, —(CH$_2$)$_n$NHCOCH$_3$, —(CH$_2$)$_n$NH$_2$, —(CH$_2$)$_n$CN, —(CH$_2$)SCH$_3$, —(CH$_2$)$_n$SO$_2$CH$_3$, —CO-lower alkyl, or —COC$_6$H$_5$;
R$^2$ is hydrogen or lower alkyl;
R$^3$ is hydrogen, nitrilo, lower alkyl, phenyl or COO-lower-alkyl;
R$^4$ is nitrilo, amino, —NHCOCH$_3$, —COC$_6$H$_5$Hal, phenyl or hydroxy;
R$^5$ is lower alkyl, —CH=CH—C$_6$H$_5$, —C$_6$H$_5$CF$_3$, —O—C(CH$_3$)$_3$ or —O-lower-alkyl;
R$^6$ is hydrogen or —COCH$_3$;
R$^7$ is —COCH$_3$, benzyl or —(CH$_2$)$_n$NHCOC$_6$H$_4$Hal; and
n is 1–3;
or a pharmaceutically acceptable acid addition salt thereof; and an inert carrier material.

11. A pharmaceutical composition according to claim 10, wherein Y$^2$ is —CH=.

12. A pharmaceutical composition according to claim 11, wherein
X is unsubstituted bicyclo[2.2.1]hept-2-yl; bicyclo[2.2.1]hept-2-yl substituted by phenyl-2-oxo-5-methoxymethyloxazolidinyl; bicyclo[2.2.1]-hept-5-en-2-yl; adamantyl; unsubstituted C$_3$–C$_7$ cycloalkyl; or C$_3$–C$_7$ cycloalkyl substituted by halogen, lower alkyl, oxo, hydroxyimino, ethylenedioxy, —OR$^1$, =CR$^2$R$^3$, —(CH$_2$)$_n$R$^4$, or —NR$^6$R$^7$,
wherein
R$^1$ is lower alkyl, hydrogen, —(CH$_2$)$_n$NH$_2$ wherein n is 3, or —(CH$_2$)$_n$CN wherein n is 2, —CO-lower alkyl, —COC$_6$H$_5$;
R$^2$ is hydrogen;
R$^3$ is hydrogen;
R$^4$ is hydroxy;
R$^6$ is H; and
R$^7$ is —(CH$_2$)$_n$NHCOC$_6$H$_4$Hal wherein n is 1–3.

13. A pharmaceutical composition according to claim 12, wherein R is hydrogen or methyl.

14. A pharmaceutical composition according to claim 13, wherein X is unsubstituted cyclohexyl; or cyclohexyl substituted by oxo, hydroxyimino, or —OR$^1$ and wherein R$^1$ is lower alkyl, hydrogen, —(CH$_2$)$_n$NH$_2$ wherein n is 3, or —(CH$_2$)$_n$CN wherein n is 2.

15. A pharmaceutical composition according to claim 12, wherein X is unsubstituted bicyclo[2.2.1]hept-2-yl or bicyclo[2.2.1]-hept-5-en-2-yl.

16. A pharmaceutical composition according to claim 11, wherein R is methyl.

17. A pharmaceutical composition according to claim 16, wherein X is cyclohexyl substituted by —OR$^1$, —(CH$_2$)$_n$R$^4$, or —COR$^5$,
wherein
R$_1$ is —(CH$_2$)$_n$NH$_2$ wherein n is 1, or —(CH$_2$)$_n$CN wherein n is 1;
R$_4$ is nitrilo and n is 1; and
R$_5$ is —CH=CH—C$_6$H$_5$.

18. A pharmaceutical composition according to claim 17, (R)-[trans-4-[4-(5-methoxymethyl-2-oxo-oxazolidin-3-yl)-phenyl]-cyclohexyloxy]-acetonitrile.

* * * * *